US012779049B2

(12) United States Patent
Gu et al.

(10) Patent No.: US 12,779,049 B2
(45) Date of Patent: Nov. 3, 2026

(54) ROS-RESPONSIVE MICRONEEDLE PATCH FOR ACNE VULGARIS TREATMENT

(71) Applicant: North Carolina State University, Raleigh, NC (US)

(72) Inventors: Zhen Gu, Los Angeles, CA (US); Yuqi Zhang, Los Angeles, CA (US)

(73) Assignee: North Carolina State University, Raleigh, NC (US)

( * ) Notice: Subject to any disclaimer, the term of this patent is extended or adjusted under 35 U.S.C. 154(b) by 1248 days.

(21) Appl. No.: 17/047,195

(22) PCT Filed: Apr. 11, 2019

(86) PCT No.: PCT/US2019/026962
§ 371 (c)(1),
(2) Date: Oct. 13, 2020

(87) PCT Pub. No.: WO2019/200081
PCT Pub. Date: Oct. 17, 2019

(65) Prior Publication Data

US 2021/0145984 A1 May 20, 2021

Related U.S. Application Data

(60) Provisional application No. 62/657,313, filed on Apr. 13, 2018.

(51) Int. Cl.
*A61K 47/69* (2017.01)
*A61K 9/00* (2006.01)
(Continued)

(52) U.S. Cl.
CPC ........ *A61K 47/6955* (2017.08); *A61K 9/0021* (2013.01); *A61K 31/155* (2013.01);
(Continued)

(58) Field of Classification Search
CPC .............. A61K 47/6955; A61K 9/0021; A61K 31/155; A61K 31/20; A61K 31/203;
(Continued)

(56) References Cited

U.S. PATENT DOCUMENTS

| | | | |
|---|---|---|---|
| 5,603,836 | A | 2/1997 | Wollrich |
| 10,653,709 | B2 | 5/2020 | Gu et al. |

(Continued)

FOREIGN PATENT DOCUMENTS

| | | | |
|---|---|---|---|
| CN | 104367940 | | 9/2017 |
| CN | 107405301 | A | 11/2017 |

(Continued)

OTHER PUBLICATIONS

Core-Shell Microneedle Gel for Self-Regulated Insulin Delivery Jinqiang Wang, Yanqi Ye, Jicheng Yu, Anna R. Kahkoska, Xudong Zhang, Chao Wang, Wujin Sun, Ria D. Corder, Zhaowei Chen, Saad A. Khan, John B. Buse, and Zhen Gu ACS Nano 2018 12 (3), 2466-2473 (Year: 2018).*

(Continued)

*Primary Examiner* — Bethany P Barham
*Assistant Examiner* — Janet Joseph
(74) *Attorney, Agent, or Firm* — Jenkins, Taylor & Hunt, P.A.

(57) ABSTRACT

A composition comprising a bioresponsive (e.g., reactive oxygen species (ROS)-responsive), antibiotic- and/or absorbent-loaded polymeric network is described. In some cases, the composition can release the antibiotic loaded therein in response to ROS or another stimulus related to inflammation. Microneedles, microneedle arrays, and skin patches comprising the composition are also described, as well as methods of treating acne or other inflammatory/infectious skin conditions.

26 Claims, 10 Drawing Sheets

(51) Int. Cl.

| | |
|---|---|
| *A61K 9/06* | (2006.01) |
| *A61K 31/155* | (2006.01) |
| *A61K 31/20* | (2006.01) |
| *A61K 31/203* | (2006.01) |
| *A61K 31/235* | (2006.01) |
| *A61K 31/7056* | (2006.01) |
| *A61K 33/06* | (2006.01) |
| *A61K 33/40* | (2006.01) |
| *A61K 38/10* | (2006.01) |
| *A61K 45/06* | (2006.01) |
| *A61K 47/02* | (2006.01) |
| *A61K 47/18* | (2017.01) |
| *A61K 47/32* | (2006.01) |
| *A61K 47/34* | (2017.01) |
| *A61K 47/36* | (2006.01) |
| *A61K 47/58* | (2017.01) |
| *A61K 47/61* | (2017.01) |
| *A61M 35/00* | (2006.01) |
| *A61M 37/00* | (2006.01) |
| *A61P 17/10* | (2006.01) |
| *A61P 31/04* | (2006.01) |

(52) U.S. Cl.

CPC ............ *A61K 31/20* (2013.01); *A61K 31/203* (2013.01); *A61K 31/235* (2013.01); *A61K 31/7056* (2013.01); *A61K 38/10* (2013.01); *A61K 45/06* (2013.01); *A61K 47/02* (2013.01); *A61K 47/32* (2013.01); *A61K 47/36* (2013.01); *A61K 47/58* (2017.08); *A61K 47/61* (2017.08); *A61K 47/6903* (2017.08); *A61M 35/006* (2013.01); *A61M 37/0015* (2013.01); *A61P 17/10* (2018.01); *A61M 2037/0023* (2013.01); *A61M 2037/0053* (2013.01); *A61M 2037/0061* (2013.01)

(58) Field of Classification Search

CPC .............. A61K 31/235; A61K 31/7056; A61K 38/10; A61K 45/06; A61K 47/02; A61K 47/32; A61K 47/36; A61K 47/58; A61K 47/61; A61K 47/6903; A61K 33/06; A61K 33/40; A61K 9/06; A61K 47/18; A61K 47/34; A61M 35/006; A61M 37/0015; A61M 2037/0023; A61M 2037/0053; A61M 2037/0061; A61M 2037/0046; A61P 17/10; A61P 31/04

See application file for complete search history.

(56) References Cited

U.S. PATENT DOCUMENTS

| | | | | |
|---|---|---|---|---|
| 11,191,815 | B2 | 12/2021 | Gu et al. | |
| 11,351,230 | B2 | 6/2022 | Gu et al. | |
| 11,813,352 | B2 | 11/2023 | Gu et al. | |
| 11,850,285 | B2 | 12/2023 | Gu et al. | |
| 2008/0268514 | A1* | 10/2008 | Muller | C12N 9/96 435/235.1 |
| 2009/0068255 | A1* | 3/2009 | Yu | A61P 35/00 424/59 |
| 2012/0244097 | A1 | 9/2012 | Lu et al. | |
| 2017/0189660 | A1* | 7/2017 | Baek | B05D 1/00 |
| 2017/0258738 | A1* | 9/2017 | DeMuth | A61K 9/5084 |
| 2021/0161968 | A1 | 6/2021 | Gu et al. | |
| 2021/0380965 | A1 | 12/2021 | Gu et al. | |
| 2022/0160841 | A1 | 5/2022 | Gu et al. | |
| 2023/0404909 | A1 | 12/2023 | Petersson et al. | |

FOREIGN PATENT DOCUMENTS

| | | | |
|---|---|---|---|
| CN | 107530296 | A | 1/2018 |
| CN | 112203664 | A | 1/2021 |
| EP | 3765029 | A1 | 1/2021 |
| KR | 20170032806 | A | 3/2017 |
| KR | 1020200144124 | A | 12/2020 |
| WO | WO2007041119 | A1 | 4/2007 |
| WO | WO 2007/092350 | A1 | 8/2007 |
| WO | WO 2008/053481 | A1 | 4/2008 |
| WO | WO 2017/143153 | A1 | 8/2017 |
| WO | WO 2017/151727 | A1 | 9/2017 |
| WO | WO 2018/106696 | A1 | 6/2018 |
| WO | WO 2019/084259 | A1 | 5/2019 |
| WO | WO 2019/200081 | A1 | 10/2019 |

OTHER PUBLICATIONS

Akamatsu., et al., “The Possible Role of Reactive Oxygen Species Generated by Neutrophils in Mediating Acne Inflammation”, in Dermatology, vol. 196, 1998, pp. 82-85.

Aktan, S., et al., “Anxiety, depression, and nature of acne vulgaris in adolescents,” Int. J. Dermatol, vol. 39, No. 5, pp. 354-357, 2000.

B. Dreno, “European recommendations on the use of oral antibiotics for acne”, in Eur. J Dermatol, vol. 14, 2004, pp. 391-399.

Bruggemann, H., et al., “The complete genome sequence of Propionibacterium acnes, a commensal of human skin,” Science, vol. 305, pp. 671-673, 2004.

Chinese Office Action corresponding to Chinese Patent Application Serial No. 2019800341948 dated Apr. 28, 2023.

Chinese Office Action corresponding to Chinese Patent Application Serial No. 2019800341948 dated Mar. 13, 2024, pp. 22.

Chinese Office Action corresponding to Chinese Patent Application Serial No. 2019800341948 dated May 17, 2024, pp. 12.

Crockett., et al., “Isotretinoin Use and the Risk of Inflammatory Bowel Disease: A Case-Control Study”, in The American journal of gastroenterology, vol. 105, 2010, pp. 1986-1993.

D. Thiboutot “An aqueous gel fixed combination of clindamycin phosphate 1.2% and benzoyl peroxide 2.5% for the once-daily treatment of moderate to severe acne vulgaris: Assessment of efficacy and safety in 2813 patients”, in .J. Am. Acad. Dermatol. 2008, vol. 59, pp. 792-800.

Dreno, B., et al., “Epidemiology of acne,” Dermatology, vol. 206, No. 7, 2003, pp. 7-10.

European Search Report corresponding to Eurpoean Patent Application Serial No. 19784620.7 dated Oct. 11, 2021.

Ghodsi, S. Z., et al., “Prevalence, severity, and severity risk factors of acne in high school pupils: a community-based study,” J. Invest. Dermatol, vol. 129, No. 9, pp. 2136-2141, 2009.

Gollnick, H. P.M., et al., “Can we define acne as a chronic disease? If so, how and when?,” Am. J. Clinical Dermatol, vol. 9, No. 5, pp. 279-284, 2008.

Gollnick, H., et al., “Topical drug treatment in acne,” Dermatology, vol. 196, No. 1, pp. 119-125, 1998.

Halvorsen, J.A., et al., “Suicidal ideation, mental health problems, and social impairment are increased in adolescents with acne: a population-based study,” J. Invest. Dermatol., vol. 131, No. 2, pp. 363-370, 2011.

International Preliminary Report on Patentability corresponding to International Patent Application Serial No. PCT/US2019/026962 dated Oct. 13, 2020.

International Search Report corresponding to International Patent Applciation Serial No. PCT/US2019/026962 dated Jul. 1, 2019.

Jacob, C.I., et al., “Acne scarring: a classification system and review of treatment options,” J Am. Acad Dermatol., vol. 45, No. 1, pp. 109-117, 2001.

Kim, J., “Review of the Innate Immune Response in Acne vulgaris: Activation of Toll-Like Receptor 2 in Acne Triggers Inflammatory Cytokine Responses,” Dermatology, vol. 211, No. 3, 2005, pp. 193-198.

Lee et al., (2008) “Dissolving Microneedles for Transdermal Drug Delivery,” Biomaterials, 29, 2113 pp. 1-23.

(56) References Cited

OTHER PUBLICATIONS

Lookingbill, et al., (1997) "Treatment of acne with a combination clindamycin/benzoyl peroxide gel compared with clindamycin gel, benzoyl peroxide gel and vehicle gel: combined results of two double-blind investigations," J. Am. Acad. Dermatol., 37, 590-595.
Lu., et al., "Bioresponsive materials", in Nature Reviews materials, vol. 2, 16075, pp. 1-17, 2017.
M. R. Prausnitz, "Microneedles for transdermal drug delivery", in Adv. Drug Del, vol. 56, 2004, pp. 581-587.
M. Rademaker, "Adverse effects of isotretinoin: A retrospective review of 1743 patients started on isotretinoin", in Australasian. J Dermatology, vol. 51, 2010, pp. 248-253.
Nagy, I., et al., "Propionibacterium acnes and lipopolysaccharide induce the expression of antimicrobial peptides and proinflammatory cytokines/chemokines in human sebocytes," Microbes infect., vol. 8, No. 8, pp. 2195-2205, 2006.
Office Action (Annex to the communication) corresponding to European Patent Application No. 19784620.7 dated Jul. 1, 2024, 4 pages.
Prausnitz., et al., "Transdermal drug delivery", in Biotechnol, vol. 26, 2008, pp. 1261-1268.
S. Briganti., et al., "Antioxidant activity, lipid peroxidation and skin diseases. What's new", in .J Eur. Acad. Dermatol. Venereol, vol. 17, 2003, 17, pp. 663-669.
Toyoda, M., et al., "Pathogenesis of acne," Med Electron Microsc., vol. 34, No. 1, 2001, pp. 29-40.
Tuchayi, S.M., et al., "Acne vulgaris," Nature Reviews Disease Primers, vol. 1, Article No. 15029, 2015.
Voss, J.G., "Acne vulgaris and free fatty acids. A review and criticism," Arch. Dermatol., vol. 109, No. 6, pp. 894-898, 1974.
Vowels, B.R., et al., "Induction of proinflammatory cytokines by a soluble factor of Propionibacterium acnes: implications for chronic inflammatory acne," Infect. Immun., vol. 63, No. 8, pp. 3158-3165, 1995.
Wang et al., (2018) "Core-Shell Microneedle Gel for Self-Regulated Insulin Delivery," ACS nano, vol. 12, No. 3 pp. 2466-2473.
Wang et al: (2018) "In situ formed reactive oxygen species-responsive scaffold with gemcitabine and checkpoint inhibitor for combination therapy". Sci. Transl. Med. vol. 10. pp. 1-13.
Webster, G.F., et al., "Characterization of serum-independent polymorphonuclear leukocyte chemotactic factors produced by Propionibacterium acnes," Inflammation, vol. 4, No. 3, 1980, pp. 261-269.
Webster, G.F., "Inflammation in acne vulgaris," J Am. Acad. Dermatol., vol. 33, pp. 247-253, 1995.
Williams, H.C., "Acne vulgaris," The Lancet, vol. 379, No. 9813, pp. 361-372, 2012.
Yazici, K., et al., "Disease-specific quality of life is associated with anxiety and depression in patients with acne," J. Eur. Acad. Dermatol. Venereol., vol. 18, No. 4, pp. 435-439, 2004.
Yu., et al., "Microneedle-array patches loaded with hypoxia-sensitive vesicles provide fast glucose-responsive insulin delivery", in Proceedings of the National Academy of Sciences, vol. 112, 2015, pp. 8260-8265.
Zhang et al., (2018) "Bioresponsive Microneedles with a Sheath Structure for H2O2 and pH Cascade-Triggered Insulin Delivery," Small, vol. 14, No. 14, full text.
Zhang et al., (2017) "Locally Induced Adipose Tissue Browning by Microneedle Patch for Obesity Treatment," ACS Nano, 11, 9223.
Zouboulis, C.C., et al., "What is the pathogenesis of acne?," Exp. Dermatol., vol. 14, No. 2, pp. 143-152, 2005.
Zouboulis, C.C., "Acne as a chronic systemic disease," Clin. Dermatol., vol. 32, No. 3, pp. 389-396, 2014.
Gollnick, H.P.M., et al., "Topical Treatment in Acne: Current Status and Future Aspects," Dermatology, vol. 206, 2003, pp. 29-36.
Korean Office Action corresponding to Korean Patent Application Serial No. 1020207032870 dated Dec. 4, 2024 (machine translation).
Saravanakumar G., et al., "Reactive-Oxygen-Species-Responsive Drug Delivery Systems: Promises and Challenges," Advanced Science, vol. 4(1), 2017, 33 Pages.
Zhang Jie; Ma Fengsen; Zhan Haohui; Huang Yingcong; (2017) "Matrix materials and their composites for dissolvable microneedle construction: a review," Materials Reports, vol. 31, No. 19, 129-134.

* cited by examiner

ROS-RESPONSIVE MICRONEEDLE PATCH FOR ACNE VULGARIS TREATMENT

RELATED APPLICATIONS

This application claims priority to and the benefit of U.S. Provisional Patent Application Ser. No. 62/657,313, filed Apr. 13, 2018; the disclosure of which is incorporated herein by reference in its entirety.

TECHNICAL FIELD

The presently disclosed subject matter relates to compositions for the bioresponsive delivery of antibiotic agents and/or compositions comprising absorbent materials. The composition can comprise a biodegradable polymer, such as a polyester, and/or a crosslinked hydrophilic polymer crosslinked with a plurality of bio-responsive linkages, wherein the composition further comprises an antibiotic or antibiotic-loaded carrier. The bioresponsive linker can be responsive to inflammation and/or reactive oxygen species (ROS). The presently disclosed subject matter further relates to microneedles, microneedle arrays, and skin patches comprising the composition; to methods of preparing the microneedle arrays; and to methods of treating acne or other inflammatory/infectious skin diseases.

Abbreviations

° C.=degrees Celsius
%=percentage
μL=microliter
m=micrometer or micron
CDM=clindamycin
CFU=colony forming units
DE=diatomaceous earth
DI=deionized
h=hour
HA=hyaluronic acid
$H_2O_2$=hydrogen peroxide
HPLC=high performance liquid chromatography
kDa=kilodalton
MBA=N,N'-methylenebisacrylamide
mg=milligram
m-HA=acrylate-modified hyaluronic acid
min=minutes
mL=milliliter
mm=millimeter
mM=millimolar
mmol=millimole
MN=microneedle
Mw=weight-average molecular weight
N=Newton
nm=nanometer
NMR=nuclear magnetic resonance
NR=non-responsive
PBA=phenylboronic acid
PBS=phosphate buffered saline
PEG=poly(ethylene glycol)
PVA=polyvinyl alcohol
RCM=reinforced clostridial medium
RhB=rhodamine B
ROS=reactive oxygen species
RR=ROS-responsive
SEM=scanning electron microscope
s.d.=standard deviation
TSPBA=$N^1$-(4-bromobenzyl)-$N^3$-(4-bromo-phenyl)-$N^1$, $N^1$,$N^3$,$N^3$-tetramethylpropane-1,3-diaminium
UV=ultraviolet
wt=weight
wt %=weight percent

BACKGROUND

Acne vulgaris (also referred to herein as "acne") is a common inflammatory skin disease associated with a colonization of *Propionibacterium acnes* (*P. acnes*) that can cause both physiological and psychological impact to the affected subject. For example, acne can cause permanent changes in skin pigmentation and scarring. It is estimated that 633 million people are affected by acne (about 85% of people 15-24 years old), making it the eighth most common disease worldwide.

More particularly, acne is associated with an overproduction of sebum, which can cause a blockage in the pilosebaceous unit, an epidermal envagination structure that includes a sebaceous gland, a hair follicle, and a follicle shaft. The blockage can cause an increased growth of *P. acnes*, leading to inflammation and other immune responses. A variety of factors, such as genetics, environmental factors, infections and hormones can contribute to acne pathogenesis.

Several types of medications have been used for treating acne, including benzoyl peroxide, retinoids, antibiotics, and hormonal agents. These agents are generally administered topically. For instance, acne is often treated through the use of topical antibiotic creams. However, these creams can have limited effect due to low drug transport to lesions within the pilosebaceous unit. Acne has also been treated by oral administration of antibiotics, but this can result in undesirable side effects, including damage to the intestinal microflora and teratogenic effects.

Accordingly, there is an ongoing need for additional compositions and methods for treating acne. In particular, there is an ongoing need for additional treatment compositions and methods that provide increased treatment efficacy and/or reduced side effects. For instance, there is an ongoing need for treatments that can provide enhanced and/or more targeted delivery of antibacterial and/or other therapeutic agents into the pilosebaceous unit, treatments that provide sustained release of effective amounts of the therapeutic agent(s), and/or treatments that can accelerate healing of the skin.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this Summary does not list or suggest all possible combinations of such features.

In some embodiments, the presently disclosed subject matter provides a composition comprising: (a) a biocompatible polymeric network comprising (i) a biodegradable polymer, optionally wherein the biodegradable polymer comprises a polyester, or (ii) a crosslinked hydrophilic polymer, wherein said crosslinked hydrophilic polymer comprises a hydrophilic polymer crosslinked via a plurality of bioresponsive linkages; and (b) one or more of (iii) an antibiotic or antibiotic-loaded carrier embedded in the biocompatible polymeric network and (iv) an absorbent additive, optionally diatomaceous earth.

In some embodiments, the antibiotic is selected from the group comprising clindamycin (CDM) or another lincosamide antibiotic; tetracycline or a tetracycline-related antibiotic, such as doxycycline, minocycline, or limecycline; trimethroprim; cotrimoxazole; erythromycin or an erythromycin-related antibiotic; and metronidazole or another nitroimidazole antibiotic. In some embodiments, the composition comprises an antibiotic and a non-antibiotic therapeutic agent, optionally wherein the non-antibiotic therapeutic agent is selected from a hormonal agent; a benzoyl peroxide formulation; a retinoid; isotretinoin; an antiandrogen; salicylic acid; azelaic acid; an antimicrobial peptide, such as omiganan pentahydrochloride; an inhibitory of a pro-inflammatory skin lipid, such as a free fatty acid; and a peroxisome proliferator-activated receptor (PPAR) modulator, such as metaformin.

In some embodiments, the biocompatible polymeric network comprises a crosslinked hydrophilic polymer and wherein one or more of the plurality of bioresponsive linkages is an inflammation-responsive linkage formed between the hydrophilic polymer and a crosslinking agent, wherein each inflammation-responsive linkage contains one or more chemical bond that is cleavable or otherwise sensitive to one or more conditions associated with inflammation, optionally wherein said one or more conditions associated with inflammation are selected from the group consisting of an increased concentration of reactive oxygen species (ROS); low pH, optionally a pH of below about 6; hypoxia; and an increased concentration of esterases or other enzymes and/or small biomolecules associated with inflammation. In some embodiments, the hydrophilic polymer is selected from the group comprising polyvinyl alcohol (PVA); a polysaccharide, optionally cellulose, hyaluronic acid (HA), dextran, alginate, cellulose, or a derivative thereof; a poly(amino acid), such as poly-L-lysine, poly-L-glutamic acid (PGS) or poly-L-serine; a protein or hydrophilic polypeptide, optionally gelatin; and a poly(alkylene glycol), optionally a poly(ethylene glycol) (PEG), polypropylene glycol (PPG), or a poly(ethylene oxide) (PEO); and linear or branched copolymers and block copolymers thereof. In some embodiments, the hydrophilic polymer is PVA or a copolymer thereof. In some embodiments, the hydrophilic polymer has a weight average molecular weight ($M_w$) of between about 10 kilodaltons (kDa) and about 200 kDa, optionally wherein the hydrophilic polymer is PVA with a $M_w$ of about 72 kDa.

In some embodiments, the inflammation-responsive linkage comprises an ester or carbamate group that is cleavable in the presence of esterases and/or a low pH environment. In some embodiments, the inflammation responsive linkage comprises a ROS-responsive linkage, optionally wherein the ROS-responsive linkage comprises an aryl boronic ester, a phenyl boronic acid or ester, a thioether, a selenium bond (e.g., a diselenium bond), a tellurium bond, a thioketal, and/or an aryl oxalate ester. In some embodiments, one or more inflammation responsive linkage comprises the structure:

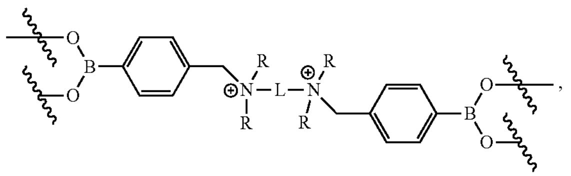

or a pharmaceutically acceptable salt thereof, wherein: each R is independently $C_1$-$C_6$ alkyl, and L is alkylene, aralkylene, or arylene, optionally propylene. In some embodiments, the crosslinked hydrophilic polymeric network is prepared by crosslinking PVA with $N^1$-(4-bromobenzyl)-$N^3$-(4-bromophenyl)-$N^1$,$N^1$,$N^3$,$N^3$,-tetramethylpropane-1,3-diaminium (TSPBA).

In some embodiments, the composition comprises between about 0 weight % and about 50 weight % of the antibiotic, optionally between about 0.1 weight % and about 50 weight % of the antibiotic. In some embodiments, the composition further comprises one or more additional treatment agent embedded in the biocompatible polymeric network, optionally wherein the one or more additional treatment agent is a skin repair agent, a wound-healing agent, or an antimicrobial agent.

In some embodiments, the presently disclosed subject matter provides a microneedle comprising a composition comprising: (a) a biocompatible polymeric network comprising (i) a biodegradable polymer, optionally wherein the biodegradable polymer comprises a polyester, or (ii) a crosslinked hydrophilic polymer, wherein said crosslinked hydrophilic polymer comprises a hydrophilic polymer crosslinked via a plurality of bioresponsive linkages; and (b) one or more of (iii) an antibiotic or antibiotic-loaded carrier embedded in the biocompatible polymeric network and (iv) an absorbent additive, optionally diatomaceous earth.

In some embodiments, the presently disclosed subject matter provides a microneedle array comprising a plurality of microneedles comprising a composition comprising: (a) a biocompatible polymeric network comprising (i) a biodegradable polymer, optionally wherein the biodegradable polymer comprises a polyester, or (ii) a crosslinked hydrophilic polymer, wherein said crosslinked hydrophilic polymer comprises a hydrophilic polymer crosslinked via a plurality of bioresponsive linkages; and (b) one or more of (iii) an antibiotic or antibiotic-loaded carrier embedded in the biocompatible polymeric network and (iv) an absorbent additive, optionally diatomaceous earth; optionally wherein each of said plurality of microneedles has a length of between about 20 and about 1000 micrometers, further optionally wherein each of the plurality of microneedles has a length of about 600 micrometers and/or a base diameter of about 300 micrometers. In some embodiments, the base of each of said plurality of microneedles is attached to a base layer comprising a crosslinked polymer and an absorbent additive, optionally wherein said absorbent additive is diatomaceous earth (DE) and/or wherein said polymer is methacrylated hyaluronic acid. In some embodiments, the base layer comprises about 10% by weight of the absorbent additive, optionally wherein the absorbent additive is selected from the group comprising aluminum silicate, aluminum starch octenylsuccinate, amylodextrin, attapulgite, bentonite, calamine, calcium silicate, cellulose, chalk, active charcoal, colloidal oatmeal, corn flour, corn starch, cyclodextrin, dextrin, diatomaceous earth, dimethylimidazolidinone corn starch, fuller's earth, hectorite, hydrated silica, silica, kaolin, loess, magnesium aluminum silicate, magnesium carbonate, magnesium hydroxide, magnesium oxide, magnesium silicate, magnesium trisilicate, maltodextrin, microcrystalline cellulose, montmorillonite, oat bran, oat flour, oat meal, potato starch, talc, wheat powder, zeolite, and combinations thereof.

In some embodiments, the microneedle array further comprises a protective backing layer attached to the base layer, optionally wherein the protective backing layer comprises a water-resistant or water-proof plastic film. In some embodiments, the microneedle array is attached to an applicator device selected from the group comprising a wand, a swab, a wipe, a pad, or a towelette.

In some embodiments, the presently disclosed subject matter provides a skin patch comprising a microneedle array of the presently disclosed subject matter, optionally wherein said patch comprises a layer comprising a skin compatible adhesive.

In some embodiments, the presently disclosed subject matter provides a method of treating acne or another inflammatory/infectious skin disease in a subject in need thereof, wherein the method comprises administering a microneedle array of the presently disclosed subject matter or a skin patch of the presently disclosed subject matter to the subject, wherein the administering comprises contacting an acne or other inflammatory/infectious skin disease-affected skin site with the array or skin patch. In some embodiments, the administering comprises contacting an affected skin site with an array of claim 19 for a period of time ranging from about 1 second to about 10 minutes. In some embodiments, the administering comprises affixing a skin patch of claim 20 to the affected site for a period of time ranging from about 15 minutes to about 7 days, optionally for a period of time ranging from about 15 minutes to 24 hours.

In some embodiments, the presently disclosed subject matter provides a method of preparing a microneedle array, wherein the method comprises: (a) providing a mold comprising one or more microcavities, optionally wherein each of the one or more microcavities is approximately conical in shape and/or wherein the microcavities have a depth of between about 300 and about 900 micrometers; (b) filing at least a portion of the one or more microcavities of the mold with a first aqueous solution comprising: (i) a hydrophilic polymer, optionally PVA or a copolymer thereof, (ii) a bioresposive crosslinking agent; and (iii) an antibiotic or antibiotic-loaded carrier and (c) drying and/or centrifuging the filled mold to deposit and/or form a crosslinked polymer matrix comprising the antibiotic embedded therein in the microcavities. In some embodiments, the method further comprises: (d) dropping a solution comprising a second polymer, optionally methacrylated hyaluronic acid (m-HA), a second crosslinking agent, an absorbent additive, optionally DE, and a photoinitator onto the dried and/or centrifuged filled mold; (e) drying the mold, optionally wherein the drying is performed in a vacuum desiccator; (f) removing the microarray from the mold; and (g) exposing the microarray to ultraviolet radiation to crosslinking the second polymer. In some embodiments, the mold comprises silicone.

In some embodiments, the presently disclosed subject matter provides a reactive oxygen species (ROS)-responsive antibiotic hydrogel comprising: (a) crosslinked hydrophilic polymer, wherein said crosslinked hydrophilic polymer comprises a hydrophilic polymer, optionally PVA or a copolymer thereof, crosslinked via a plurality of ROS-responsive linkages, wherein each of the ROS-responsive linkages comprises one or more bond that is cleavable in the presence of a ROS, optionally wherein the ROS is a peroxide; and (b) an antibiotic or antibiotic-loaded carrier embedded in the biocompatible polymeric network, optionally wherein the antibiotic is clindamycin.

In some embodiments, the ROS-responsive linkages each comprise an aryl boronic ester. In some embodiments, the ROS-responsive linkages each comprise the structure:

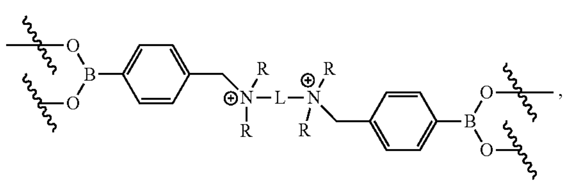

or a pharmaceutically acceptable salt thereof, wherein: each R is independently $C_1$-$C_6$ alkyl, and L is alkylene, aralkylene, or arylene, optionally propylene.

In some embodiments, the crosslinked hydrophilic polymeric network is prepared by crosslinking PVA or a copolymer thereof with N-(4-bromobenzyl)-$N^3$-(4-bromophenyl)-$N^1$,$N^1$,$N^3$,$N^3$,-tetramethylpropane-1,3-diaminium (TSPBA) in the presence of the antibiotic. In some embodiments, the crosslinking is performed by mixing the PVA with the TSPBA in a molar ratio of between about 20:1 to about 1:5, optionally about 3:1.

In some embodiments, the composition comprises between about 0.1 weight % and about 50 weight % of the antibiotic.

In some embodiments, the presently disclosed subject matter provides a microneedle comprising a reactive oxygen species (ROS)-responsive antibiotic hydrogel comprising: (a) crosslinked hydrophilic polymer, wherein said crosslinked hydrophilic polymer comprises a hydrophilic polymer, optionally PVA or a copolymer thereof, crosslinked via a plurality of ROS-responsive linkages, wherein each of the ROS-responsive linkages comprises one or more bond that is cleavable in the presence of a ROS, optionally wherein the ROS is a peroxide; and (b) an antibiotic or antibiotic-loaded carrier embedded in the biocompatible polymeric network, optionally wherein the antibiotic is clindamycin.

In some embodiments, the presently disclosed subject matter provides a microneedle array comprising a plurality of microneedles comprising a reactive oxygen species (ROS)-responsive antibiotic hydrogel comprising: (a) crosslinked hydrophilic polymer, wherein said crosslinked hydrophilic polymer comprises a hydrophilic polymer, optionally PVA or a copolymer thereof, crosslinked via a plurality of ROS-responsive linkages, wherein each of the ROS-responsive linkages comprises one or more bond that is cleavable in the presence of a ROS, optionally wherein the ROS is a peroxide; and (b) an antibiotic or antibiotic-loaded carrier embedded in the biocompatible polymeric network, optionally wherein the antibiotic is clindamycin. In some embodiments, the microneedle array further comprises a base layer attached to the base of each of the plurality of microneedles, wherein the base layer comprises a crosslinked polymer and an absorbent material, optionally diatomaceous earth.

In some embodiments, the presently disclosed subject matter provides a skin patch or swab comprising a microneedle array comprising a plurality of microneedles comprising a reactive oxygen species (ROS)-responsive antibiotic hydrogel comprising: (a) crosslinked hydrophilic polymer, wherein said crosslinked hydrophilic polymer comprises a hydrophilic polymer, optionally PVA or a copolymer thereof, crosslinked via a plurality of ROS-responsive linkages, wherein each of the ROS-responsive linkages comprises one or more bond that is cleavable in the presence of a ROS, optionally wherein the ROS is a peroxide; and (b) an antibiotic or antibiotic-loaded carrier embedded in the biocompatible polymeric network, optionally wherein the antibiotic is clindamycin.

In some embodiments, the presently disclosed subject matter provides a microneedle array comprising: (a) a plurality of microneedles comprising a biocompatible polymeric network comprising (i) a biodegradable polymer, optionally wherein the biodegradable polymer comprises a polyester, or (ii) a crosslinked hydrophilic polymer, wherein said crosslinked hydrophilic polymer comprises a hydrophilic polymer crosslinked via a plurality of bioresponsive linkages, optionally wherein each of said plurality of microneedles has a length of between about 20 and about 1000 micrometers, further optionally wherein each of the plurality of microneedles has a length of about 600 micrometers and/or a base diameter of about 300 micrometers; (b) a base layer to which a base of each of said plurality of microneedles is attached and wherein said base layer comprises a crosslinked polymer, optionally wherein the crosslinked polymer is methacrylated hyaluronic acid; and (c) an absorbent, optionally wherein the absorbent is present in the base layer.

In some embodiments, the base layer comprises about 10% by weight of the absorbent, optionally wherein the absorbent additive is selected from the group comprising aluminum silicate, aluminum starch octenylsuccinate, amylodextrin, attapulgite, bentonite, calamine, calcium silicate, cellulose, chalk, active charcoal, colloidal oatmeal, corn flour, corn starch, cyclodextrin, dextrin, diatomaceous earth, dimethylimidazolidinone corn starch, fuller's earth, hectorite, hydrated silica, silica, kaolin, loess, magnesium aluminum silicate, magnesium carbonate, magnesium hydroxide, magnesium oxide, magnesium silicate, magnesium trisilicate, maltodextrin, microcrystalline cellulose, montmorillonite, oat bran, oat flour, oat meal, potato starch, talc, wheat powder, zeolite, and combinations thereof. In some embodiments, the absorbent is diatomaceous earth.

In some embodiments, the plurality of microneedles comprise a crosslinked hydrophilic polymer and wherein one or more of the plurality of bioresponsive linkages is an inflammation-responsive linkage formed between the hydrophilic polymer and a crosslinking agent, wherein each inflammation-responsive linkage contains one or more chemical bond that is cleavable or otherwise sensitive to one or more conditions associated with inflammation, optionally wherein said one or more conditions associated with inflammation are selected from the group consisting of an increased concentration of reactive oxygen species (ROS); low pH, optionally a pH of below about 6; hypoxia; and an increased concentration of esterases or other enzymes and/or small biomolecules associated with inflammation. In some embodiments, the hydrophilic polymer is selected from the group comprising polyvinyl alcohol (PVA); a polysaccharide, optionally cellulose, hyaluronic acid (HA), dextran, alginate, cellulose, or a derivative thereof; a poly(amino acid), such as poly-L-lysine, poly-L-glutamic acid (PGS) or poly-L-serine; a protein or hydrophilic polypeptide, optionally gelatin; and a poly(alkylene glycol), optionally a poly (ethylene glycol) (PEG), polypropylene glycol (PPG), or a poly(ethylene oxide) (PEO); and linear or branched copolymers and block copolymers thereof. In some embodiments, the crosslinked hydrophilic polymeric network is prepared by crosslinking PVA or a copolymer thereof with $N^1$-(4-bromobenzyl)-$N^3$-(4-bromophenyl)-$N^1$,$N^1$,$N^3$,$N^3$,-tetramethylpropane-1,3-diaminium (TSPBA).

In some embodiments, the microneedle array further comprises a protective backing layer attached to the base layer, optionally wherein the protective backing layer comprises a water-resistant or water-proof plastic film. In some embodiments, the microneedle array is attached to an applicator device selected from the group comprising a wand, a swab, a wipe, a pad, or a towelette.

In some embodiments, the presently disclosed subject matter provides a skin patch comprising a microneedle array comprising: (a) a plurality of microneedles comprising a biocompatible polymeric network comprising (i) a biodegradable polymer, optionally wherein the biodegradable polymer comprises a polyester, or (ii) a crosslinked hydrophilic polymer, wherein said crosslinked hydrophilic polymer comprises a hydrophilic polymer crosslinked via a plurality of bioresponsive linkages, optionally wherein each of said plurality of microneedles has a length of between about 20 and about 1000 micrometers, further optionally wherein each of the plurality of microneedles has a length of about 600 micrometers and/or a base diameter of about 300 micrometers; (b) a base layer to which a base of each of said plurality of microneedles is attached and wherein said base layer comprises a crosslinked polymer, optionally wherein the crosslinked polymer is methacrylated hyaluronic acid; and (c) an absorbent, optionally wherein the absorbent is present in the base layer; optionally wherein said patch comprises a layer comprising a skin compatible adhesive.

In some embodiments, the presently disclosed subject matter provides a method of treating acne or another inflammatory/infectious skin disease in a subject in need thereof, wherein the method comprises administering a microneedle array comprising: (a) a plurality of microneedles comprising a biocompatible polymeric network comprising (i) a biodegradable polymer, optionally wherein the biodegradable polymer comprises a polyester, or (ii) a crosslinked hydrophilic polymer, wherein said crosslinked hydrophilic polymer comprises a hydrophilic polymer crosslinked via a plurality of bioresponsive linkages, optionally wherein each of said plurality of microneedles has a length of between about 20 and about 1000 micrometers, further optionally wherein each of the plurality of microneedles has a length of about 600 micrometers and/or a base diameter of about 300 micrometers; (b) a base layer to which a base of each of said plurality of microneedles is attached and wherein said base layer comprises a crosslinked polymer, optionally wherein the crosslinked polymer is methacrylated hyaluronic acid; and (c) an absorbent, optionally wherein the absorbent is present in the base layer, or a skin patch comprising the microneedle array to the subject, wherein the administering comprises contacting an acne or other inflammatory/infectious skin disease-affected skin site with the array or skin patch.

Accordingly, it is an object of the presently disclosed subject matter to provide bio-responsive compositions and devices for the delivery of medications and/or absorbents to treat acne or other inflammatory/infectious skin conditions, as well as methods of preparing and using said compositions and devices.

An object of the presently disclosed subject matter having been stated hereinabove, and which is achieved in whole or in part by the presently disclosed subject matter, other objects will become evident as the description proceeds when taken in connection with the accompanying drawings and examples as best described herein below.

DETAILED DESCRIPTION

Figure 1A:
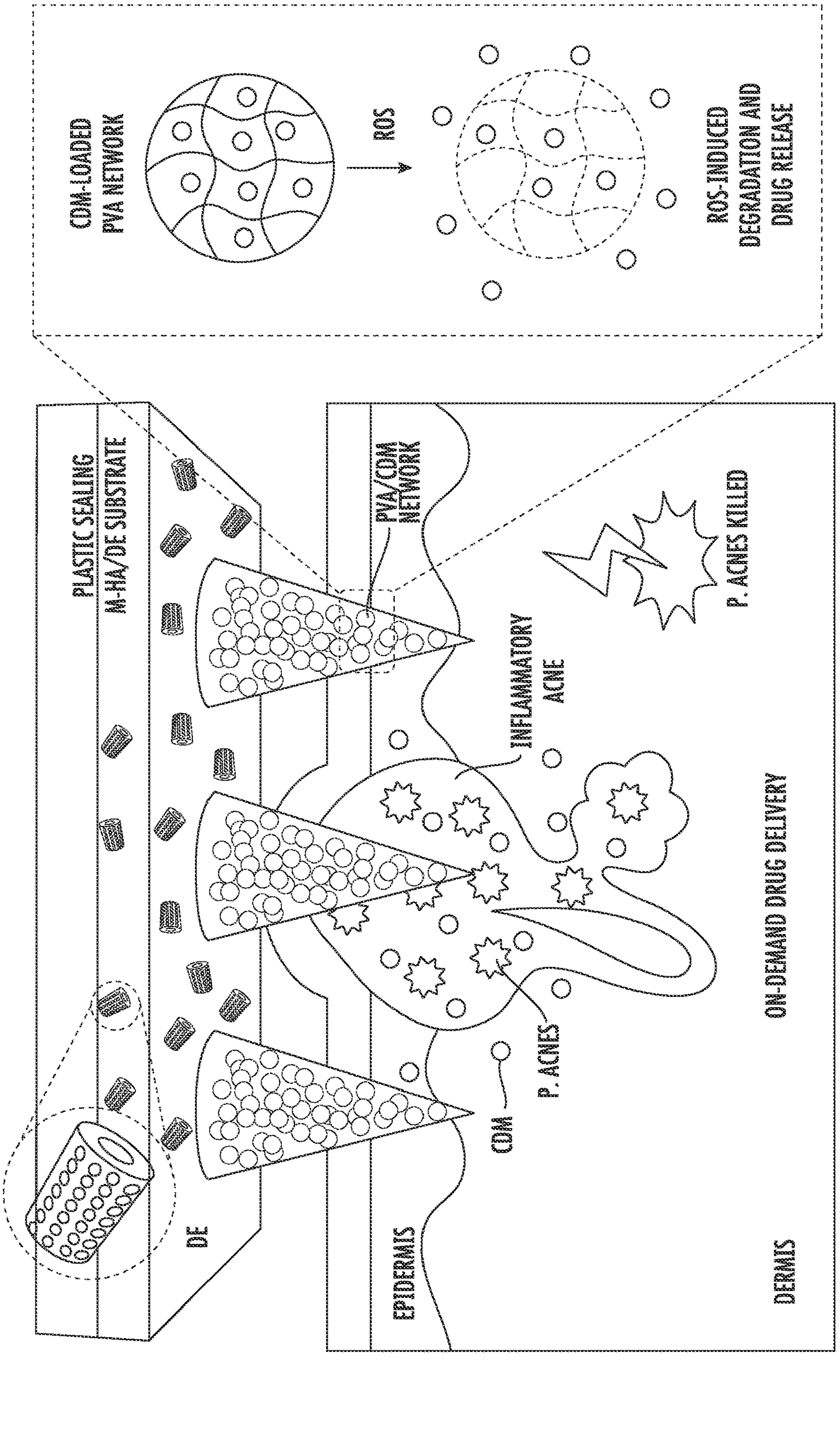
FIG. 1A is a schematic drawing of the formation and mechanism of a reactive oxygen species (ROS)-responsive microneedle skin patch for acne vulgaris treatment according to the presently disclosed subject matter. On the left is shown a schematic drawing of a skin patch comprising microneedles filled with a clindamycin (CDM)-loaded polyvinyl alcohol (PVA) network (PVA/CDM network). The microneedles are attached to a substrate comprising a layer of acrylate-modified hyaluronic acid (m-HA) further comprising diatomaceous earth (DE) (indicated by shaded cylinders) backed by a plastic sealing layer. When the microneedles penetrate the skin and are in contact with an *P. acnes*-infected follicle, CDM (filled circles) is released from the PVA-CDM network in response to ROS, killing the acne (shaded sun shapes). The inset drawing at the right further illustrates the ROS-based release mechanism of the CDM-loaded PVA network. CDM is again indicated by filled circles, intact crosslinked PVA network is indicated by wavy lines, and biodegraded PVA network by dotted lines.

The presently disclosed subject matter will now be described more fully hereinafter with reference to the accompanying Examples and Drawings, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which the presently described subject matter belongs. All publications, patent applications, patents, and other references mentioned herein are incorporated by reference in their entirety.

Throughout the specification and claims, a given chemical formula or name shall encompass all active optical and stereoisomers, as well as racemic mixtures where such isomers and mixtures exist.

I. Definitions

While the following terms are believed to be well understood by one of ordinary skill in the art, the following definitions are set forth to facilitate explanation of the presently disclosed subject matter.

Following long-standing patent law convention, the terms "a", "an", and "the" refer to "one or more" when used in this application, including the claims. Thus, for example, reference to "a composition" or "a polymer" includes a plurality of such compositions or polymers, and so forth.

Unless otherwise indicated, all numbers expressing quantities of size, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about", when referring to a value or to an amount of size (i.e., diameter), weight, time, dose, concentration or percentage is meant to encompass variations of in one example ±20% or ±10%, in another example ±5%, in another example ±1%, and in still another example ±0.1% from the specified amount, as such variations are appropriate to perform the disclosed methods.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

The term "comprising", which is synonymous with "including" "containing" or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. In some embodiments, "lower alkyl" can refer to $C_{1-6}$ or $C_{1-5}$ alkyl groups. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, nitro, amino, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

The term "aralkyl" refers to an -alkyl-aryl group, optionally wherein the alkyl and/or aryl group comprises one or more alkyl and/or aryl group substituents.

In some embodiments, the term "bivalent" refers to a group that can bond (e.g., covalently bond) or is bonded to two other groups, such as other alkyl, aralkyl, cycloalkyl, or aryl groups. Typically, two different sites on the bivalent group (e.g., two different atoms) can bond to groups on other molecules. For example, the bivalent group can be an alkylene group.

A wavy line through a bond indicates the site where one chemical group can be attached (i.e., be bonded to) to another, unshown group.

"Alkylene" can refer to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene ($-CH_2-$); ethylene ($-CH_2-CH_2-$); propylene ($-(CH_2)_3-$); cyclohexylene ($-C_6H_{10}-$); $-CH{=}CH-CH{=}CH-$; $-CH{=}CH-CH_2-$; $-(CH_2)_q-N(R)-(CH_2)_r-$, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl ($-O-CH_2-O-$); and ethylenedioxyl ($-O-(CH_2)_2-O-$). An alkylene group can have about 2 to about 3 carbon atoms and can further have 6-20 carbons.

"Arylene" refers to a bivalent aryl group, which can be substituted or unsubstituted.

The term "aralkylene" refers to a bivalent group that comprises a combination of alkylene and arylene groups (e.g., -arylene-alkylene-, alkylene-arylene-alkylene-, arylene-alkylene-arylene-, etc.).

The terms "amino" and "amine" as used herein refer to the group $-N(R)_2$ wherein each R is independently H, alkyl, substituted alkyl, aryl, substituted aryl, aralkyl, or substituted aralkyl. The terms "aminoalkyl" and "alkylamino" can refer to the group $-R'-N(R)_2$ wherein each R is H, alkyl, substituted alkyl, aralkyl, substituted aralkyl, aryl, or substituted aryl, and wherein R' is alkylene. "Arylamine" and "aminoaryl" refer to the group $-R'-N(R)_2$ wherein each R is H, alkyl, substituted alkyl, aralkyl, substituted aralkyl, aryl, or substituted aryl, and R' is arylene. The term "primary amine" refers to a group comprising a $-NH_2$ group.

The term "ammonium" as used herein refers to the group formed from a positively charged, tetra-substituted nitrogen, i.e., $-R'^{+}N(R)_3$ wherein each R is independently H, alkyl, substituted alkyl, aryl, substituted aryl, aralkyl, or substituted aralkyl and R' is alkylene, aralkylene or arylene. In some embodiments, the term "ammonium" refers to the positively charged group formed by the protonation of an amine group. In some embodiments, the term "ammonium" or "aminium" refers to a positively-charged, protonated primary amine group, i.e., a $-^{+}NH_3$ group.

The terms "halo", "halide", or "halogen" as used herein refer to fluoro, chloro, bromo, and iodo groups.

The term "hydroxyl" refers to the $-OH$ group.

The term "alkoxy" refers to a $-OR$ group, wherein R is alkyl or substituted alkyl.

The terms "carboxylate" and "carboxylic acid" can refer to the groups $-C(=O)O^-$ and $-C(=O)OH$, respectively. In some embodiments, "carboxylate" can refer to either the $-C(=O)O-$ or $-C(=O)OH$ group.

The term "ester" as used herein can refer to the group having the formula $R-C(=O)-OR'$, wherein R and R' are independently selected from alkyl, substituted alkyl, aralkyl, substituted aralkyl, aryl, and substituted aryl.

The term "carbamate" as used herein can refer to the group having the formula $R-NR'-C(=O)-OR''$, wherein R and R'' are independently selected from alkyl, substituted alkyl, aralkyl, substituted aralkyl, aryl, and substituted aryl; and wherein R' is H, alkyl, substituted alkyl, aralkyl, substituted aralkyl, aryl, or substituted aryl.

The term "boronic acid" as used herein refers to a group having the formula $-B-(OH)_2$.

The terms "boronic acid ester" and "boronic ester" as used herein refer to a boronic acid wherein the hydrogen atom of each of the OH groups is replaced by a monovalent carbon group independently selected from alkyl, substituted alkyl, aralkyl, substituted aralkyl, aryl, or substituted aryl. In some embodiments, each of the hydrogen atoms is replaced by a monovalent group on a polymer chain. The terms "aryl boronic acid ester" and "aryl boronic ester" as used herein refer to a boronic acid ester wherein the boron atom is directly attached to an aryl group, e.g., phenyl.

The term "microneedle" as used herein refers to a needle-like structure having at least one region (e.g., length, base diameter, etc.) with a dimension of less than about 1,000 microns (μm). In some embodiments, the term "microneedle" refers to a structure having a dimension between about 1 micron and about 1,000 microns (e.g., about 1, 5, 10, 25, 50, 75, 100, 200, 300, 400, 500, 600, 700, 800, 900 or about 1,000 microns). A microneedle can have a conical or pyramidal shape or can be substantially rod-shaped, but have one end/tip comprising a conical- or pyramidal-shaped structure.

As used herein, a "macromolecule" refers to a molecule of high relative molecular mass, the structure of which comprises the multiple repetition of units derived from molecules of low relative molecular mass, e.g., monomers and/or oligomers.

An "oligomer" refers to a molecule of intermediate relative molecular mass, the structure of which comprises a small plurality (e.g., 2, 3, 4, 5, 6, 7, 8, 9, or 10) of repetitive units derived from molecules of lower relative molecular mass.

As used herein, a "monomer" refers to a molecule that can undergo polymerization, thereby contributing constitutional units, i.e., an atom or group of atoms, to the essential structure of a macromolecule.

The terms "polymer" and "polymeric" refer to chemical structures that have repeating constitutional units (i.e., multiple copies of a given chemical substructure or "monomer unit"). As used herein, polymers can refer to groups having more than 10 repeating units and/or to groups wherein the repeating unit is other than methylene. Polymers can be formed from polymerizable monomers. A polymerizable monomer is a molecule that comprises one or more reactive moieties {e.g., siloxy ethers, hydroxyls, amines, vinylic groups (i.e., carbon-carbon double bonds), halides (i.e., Cl, Br, F, and I), carboxylic acids, esters, activated esters, and the like} that can react to form bonds with other molecules. Generally, each polymerizable monomer molecule can bond to two or more other molecules. In some cases, a polymerizable monomer will bond to only one other molecule, forming a terminus of the polymeric material. Some polymers contain biodegradable linkages, such as esters or amides, such that they can degrade over time under biological conditions (e.g., at a certain pH present in vivo, in a hypoxic environment, or in the presence of enzymes or small biomolecules, e.g., that are present in one or more particular biological environments or are generated in one or more particular biological environments under certain conditions, e.g., disease, stress, etc.).

A "copolymer" refers to a polymer derived from more than one species of monomer. Each species of monomer provides a different species of monomer unit.

Polydispersity (PDI) refers to the ratio ($M_w/M_n$) of a polymer sample. $M_w$ refers to the mass average molar mass (also commonly referred to as weight average molecular weight). $M_n$ refers to the number average molar mass (also commonly referred to as number average molecular weight).

"Biocompatible" as used herein, generally refers to a material and any metabolites or degradation products thereof that are generally non-toxic to the recipient (e.g., an animal, such as a human or other mammal) and do not cause any significant adverse effects to the recipient.

"Biodegradable" as used herein, generally refers to a material that will degrade or erode under physiologic conditions to form smaller units or chemical species that are capable of being metabolized, eliminated, or excreted by the subject. In some embodiments, the degradation time is a function of polymer composition and/or morphology. Suitable degradation times are from days to weeks. For example, in some embodiments, the polymer can degrade over a time period from seven days to 24 weeks, optionally seven days to twelve weeks, optionally from seven days to six weeks, or further optionally from seven days to three weeks.

The term "hydrophilic" can refer to a group that dissolves or preferentially dissolves in water and/or aqueous solutions.

The term "hydrophobic" refers to groups that do not significantly dissolve in water and/or aqueous solutions and/or which preferentially dissolve in fats and/or non-aqueous solutions.

The terms "cross-linking reagent" or "cross-linking agent" as used herein refer to a compound that includes at least two reactive functional groups (or groups that can be deblocked or deprotected to provide reactive functional groups), which can be the same or different. In some embodiments, the two reactive functional groups can have different chemical reactivity (e.g., the two reactive functional groups are reactive (e.g., form bonds, such as covalent bonds) with different types of functional groups on other molecules, or one of the two reactive functional groups tends to react more quickly with a particular functional group on another molecule than the other reactive functional group). Thus, the cross-linking reagent can be used to link (e.g., covalently bond) two other entities (e.g., molecules, polymers, proteins, nucleic acids, vesicles, liposomes, nanoparticles, microparticles, etc.) or to link two groups on the same entity (e.g., a polymer) to form a cross-linked composition.

The term "crosslinked polymer" as used herein refers to a polymer comprising at least one and typically more than one additional bonds formed between sites on an individual polymer chain and/or between individual polymer chains. In some embodiments, the sites are bonded to one another via a linker group formed when a crosslinking agent bonds to two different sites on a polymer chain or to sites on two different polymer chains.

The term "bioresponsive" as used herein refers to the sensitivity of a composition or chemical linkage to particular biologically relevant signals. For example, a "bioresponsive" material can undergo structural and/or morphological changes in response to a one or more particular biological stimulus, such as, but not limited to, a particular pH, temperature, and/or the presence of one or more particular biological molecules, e.g., an enzyme or other molecule present under particular biological conditions (e.g., the presence of a particular disease state or in a particular biological tissue). In some embodiments, "bioresponsive linkage" refers to a bivalent chemical moiety that contains one or more bonds (e.g., one or more covalent bonds) that are cleaved and/or transformed in the presence of a particular biological stimulus. In some embodiments, the linkage is cleaved. In some embodiments, such as when the bivalent chemical moiety contains one or more bonds that are oxidized or reduced in the presence of a particular biological condition or conditions, the nature of the bivalent linkage can be altered, e.g., from hydrophobic to hydrophilic.

In some embodiments, the bioresponsive material or linkage is an "inflammation-responsive" material or linkage, which is sensitive to a biological stimulus present in a tissue as the result of the inflammatory response. Such stimulus include, but are not limited to low pH (e.g., a pH lower than about 6 or a pH between about 5 and about 6); hypoxia; the increased presence of reactive oxygen species (ROS) and/or reactive nitrogen species (RNS) or another small biomolecule, and increased enzymatic activity (e.g., increased esterase activity) and/or the presence of a small biomolecule (e.g., a small molecule generated in a biological cell or tissue). In some embodiments, the material or linkage is a "ROS-responsive" material or linkage that is sensitive to one or more reactive oxygen species, e.g., hydrogen peroxide or another peroxide, superoxide, hydroxyl radical, and singlet oxygen.

II. Compositions and Methods for the Treatment of Skin Conditions

The presently disclosed subject matter relates, in some embodiments, to compositions for the targeted delivery of therapeutic agents to treat skin diseases and disorders, particularly inflammatory and/or infection-related skin diseases or disorders, such as, but not limited to acne, contact dermatitis (e.g., seborrheic, atopic, diaper, infections eczematoid, or light sensitive dermatitis), eczema, folliculitis, cellulitis, impetigo, boils, clavus, and psoriasis. In some embodiments, the presently disclosed subject matter relates to a bioresponsive crosslinked polymer matrix that can be used to prepare a microneedle and/or a microneedle array for the delivery of an antibiotic (and optionally one or more additional therapeutic agent) and/or an absorbent additive that is loaded in the matrix to the site of an acne flare up or to the active site of another skin condition, such as, but not limited to, contact dermatitis (e.g., seborrheic, atopic, diaper, infections eczematoid, or light sensitive dermatitis), eczema, folliculitis, cellulitis, impetigo, boils, clavus, psoriasis, and other inflammatory skin conditions and/or skin infections. In some embodiments, a microneedle array or a device containing such an array can be used to extract tissue fluid (e.g., comprising cells, bacteria, viral particles, biomolecules, biomarkers, toxins, and/or other small molecules) for sampling of disease sites and further analysis.

Thus, in some embodiments, the presently disclosed subject matter provides a composition comprising: (a) a biocompatible polymeric network and (b) one or more of (i) an antibiotic (i.e., an antibacterial agent) or antibiotic-loaded carrier (e.g., an antibiotic-loaded liposome, polymersome, nanoparticle, or microparticle) embedded in the biocompatible polymeric network, and (ii) an absorbent additive. In some embodiments, the presently disclosed subject matter provides a composition comprising: (a) a biocompatible polymeric network and (b) an antibiotic (i.e., an antibacterial agent) or antibiotic-loaded carrier (e.g., an antibiotic-loaded liposome, polymersome, nanoparticle, or microparticle) embedded in the biocompatible polymeric network.

In some embodiments, the biocompatible polymeric network comprises a biodegradable biocompatible polymer, such as, but not limited to, a polyester. Thus, in some embodiments, the embedded therapeutic agent (e.g., the antibiotic) is released from the matrix as the biodegradable polymer degrades. Alternatively, in some embodiments, the biocompatible polymeric network comprises a crosslinked hydrophilic polymer that comprises a hydrophilic polymer crosslinked via a plurality of bioresponsive linkages. Thus, in some embodiments, the embedded therapeutic agent is released from the matrix as the bioresponsive linkages are cleaved or otherwise transformed. In some embodiments, the bioresponsive linkages are cleaved and the matrix becomes less crosslinked and thus, more "leaky." In some embodiments, the biocompatible polymeric network comprises a biodegradable polymer that is crosslinked with bioresponsive linkages and the therapeutic agent is released in response to both the degradation of the polymer and the reduction of its crosslinking.

Accordingly, the presently disclosed compositions can comprise at least one antibiotic. Any suitable antibiotic can be used, such as an antibiotic known in the art for the treatment of acne or another skin infection. In some embodiments, the antibiotic is selected from the group comprising clindamycin (CDM) or another lincosamide antibiotic; tetracycline or a tetracycline-related antibiotic, such as doxycycline, minocycline, or limecycline; trimethroprim; cotrimoxazole; erythromycin or an erythromycin-related antibiotic; and metronidazole or another nitroimidazole antibiotic. In some embodiments, the antibiotic is provided within or otherwise associated with a carrier (e.g., a liposome, polymersome, nanoparticle or microparticle). In some embodiments, the composition comprises an antibiotic and a non-antibiotic skin condition therapeutic agent. In some embodiments, the non-antibiotic skin condition therapeutic agent is selected from the group including, but not limited to, a hormonal agent, benzoyl peroxide or a related formulation, a retinoid, isotretinoin, an antiandrogen, salicylic acid, azelaic acid, an antimicrobial peptide (e.g., omiganan pentahydrochloride), an inhibitor of a pro-inflammatory skin lipid, such as a free fatty acid, and a PPAR modulator, such as metaformin. In some embodiments, the non-antibiotic skin condition therapeutic agent can be another antimicrobial agent (e.g., an anti-viral agent, an anti-fungal agent, or an anti-parasite agent) or an anti-inflammatory agent. In some embodiments, the composition can further comprise another therapeutic agent, such as a skin repair agent, a wound-healing agent, or an analgesic.

In some embodiments, the biocompatible polymeric network comprises a crosslinked hydrophilic polymer that comprises a plurality of inflammation-responsive linkages formed between the hydrophilic polymer and a crosslinking agent. For example, each inflammation-responsive linkage can contain one or more chemical bond that is cleavable under one or more conditions associated with inflammation, optionally wherein said one or more conditions associated with inflammation are selected from the group comprising an increased concentration of reactive oxygen species (ROS); a low pH (e.g., a pH of below about 6 or a pH of between about 5 and 6); a hypoxic environment; and an increased concentration of esterases or other enzymes and/or small biomolecules associated with an inflammatory response.

Any suitable biocompatible hydrophilic polymer can be used. The polymer can be a natural polymer or a synthetic polymer. In some embodiments, the hydrophilic polymer is selected from the group including, but not limited to, polyvinyl alcohol (PVA) or a copolymer thereof; a polysaccharide, optionally hyaluronic acid (HA), dextran, alginate, cellulose or a derivative thereof; a protein or hydrophilic polypeptide, optionally gelatin; a poly(amino acid), such as poly-L-lysine, poly-L-glutamic acid, or poly-L-serine; and a poly(alkylene glycol), optionally a poly(ethylene glycol) (PEG), polypropylene glycol (PPG), or poly(ethylene oxide) (PEO); as well as linear and branched copolymers and block copolymers thereof. In some embodiments, the hydrophilic polymer is PVA or a copolymer thereof. In some embodiments, the PVA or other polymer has a weight average molecular weight ($M_w$) of between about 10 kDa and about 200 kDa (e.g., about 10, 25, 50, 75, 100, 125, 150, 175, or about 200 kDa). In some embodiments, the PVA has a $M_w$ of about 72 kDa.

In some embodiments, the inflammation-responsive linkages can comprise one or more ester or carbamate groups that can be cleaved by an esterase or via acid-catalyzed hydrolysis (i.e., in a low pH aqueous environment). In some embodiments, the inflammation responsive linkage comprises a ROS-responsive linkage. In some embodiments, the ROS-responsive linkage comprises an aryl boronic ester, a phenyl boronic acid or ester, a thioether, a selenium bond (e.g., a diselenium bond), a tellurium bond, a thioketal, and/or an aryl oxalate ester. In some embodiments, the ROS-responsive linkage comprises an aryl boronic ester. For instance, the bivalent linkage resulting from reaction of the crosslinking agent and the polymer can have a structure of, for example:

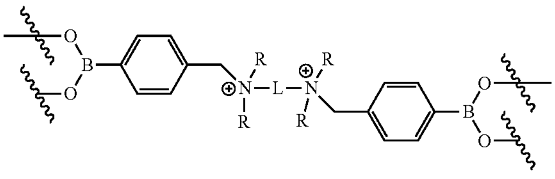

wherein each R is independently $C_1$-$C_6$ alkyl, and L is alkylene, aralkylene, or arylene. In some embodiments, each R is methyl. In some embodiments, L is propylene (i.e., $-CH_2CH_2CH_2-$). In some embodiments, the linker can be provided in the form of a pharmaceutically acceptable salt and include one or two anions (e.g., a halide anion) to balance the charge of the aminium ions. The linkage can be the result of the reaction of hydroxyl groups on a polymer chain with the hydroxyl groups of boronic acid moieties in the crosslinking agent. Thus, for instance, each of the four oxygen atoms of the structure shown above can be covalently attached to carbon atoms in a polymer chain. In some embodiments, the crosslinked hydrophilic polymeric network is prepared by crosslinking PVA with $N^1$-(4-bromobenzyl)-$N^3$-(4-bromophenyl)-$N^1$,$N^1$,$N^3$,$N^3$-tetramethylpropane-1,3-diaminium (TSPBA).

The amount of crosslinking agent can be varied depending upon the rate of delivery of the therapeutic agent desired and/or the target mechanical strength of the resulting matrix material. In some embodiments, the more crosslinking agent used, the slower the rate of drug delivery. In some embodiments, the ratio of polymer to crosslinking agent is between about 20:1 to about 1:5 (e.g., about 20:1, 18:1, 16:1, 14:1, 12:1, 10:1, 8:1, 6:1, 5:1, 4:1, 3:1, 2:1, 1:1, 1:2, 1:3, 1:4, or about 1:5). In some embodiments, the ratio of polymer to crosslinking agent is about 3:1. In some embodiments, the amount of crosslinking agent is adjusted to provide sustained release of a therapeutically effect amount of the therapeutic agent when the composition is in contact with an active disease site (e.g., when the composition is in contact with inflamed tissue).

The presently disclosed composition can comprise between 0 weight % and about 50 weight % of the antibiotic. When the antibiotic is present, the rate of drug delivery can also be adjusted by varying the amount of therapeutic agent or agents embedded in the matrix. In some embodiments, the composition comprises between about 0.1 weight % and about 50 weight % of an antibiotic. In some embodiments, the composition comprises about 0.1, 0.5, 1.0, 2.5, 5.0, 10, 15, 20, 25, 30, 35, 40, 45, or 50% of the antibiotic by weight.

In some embodiments, the presently disclosed subject matter provides a microneedle comprising a composition as disclosed herein. A representative embodiment is shown schematically in FIG. 1A. In some embodiments, the presently disclosed subject matter provides a microneedle array comprising a plurality of such microneedles. For example, in some embodiments, the presently disclosed subject matter provides a microneedle array comprising a plurality of microneedles comprising a bioresponsive (e.g., inflammation-responsive and/or ROS-responsive) crosslinked polymer and an antibiotic. In some embodiments, the microneedle array can comprise a plurality of microneedles wherein each of said plurality of microneedles has a length of between about 20 and about 1000 microns (e.g., about 20, 50, 100, 150, 200, 250, 300, 350, 400, 450, 500, 550, 600, 650, 700, 750, 800, 850, 900, 950, or about 1000 microns). In some embodiments, each of the plurality of microneedles has a length of between about 500 microns and about 700 microns. In some embodiments, each of the plurality of microneedles has a length of about 600 microns.

Figure 3B:
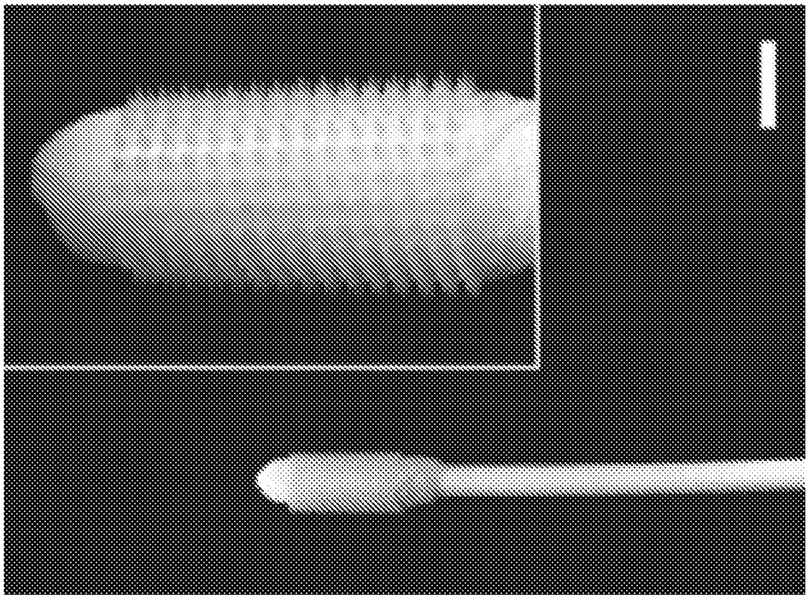
FIG. 3B is a photograph of a microneedle patch attached to a cotton stick. The inset at the top shows a closer view of the patch attached at the top of the stick. The white scale bar in the lower right of the photograph represents 10 centimeters.
Figure 3A:
FIG. 3A is a scanning electron microscope (SEM) image of a microneedle array according to the presently disclosed subject matter. The black scale bar in the lower right-hand corner of the image represents 200 microns.

In some embodiments, such as shown in FIG. 1A and FIG. 3A, each microneedle can have an approximately conical or pyramidal shape. In some embodiments, the base of each microneedle can be between about 10 and about 600 microns (e.g., about 20, 50, 75, 100, 150, 200, 250, 300, 350, 400, 450, 500, 550, or about 600 microns) in diameter. In some embodiments, the diameter of each microneedle base can be between about 200 and about 400 microns. In some embodiments, the diameter of each microneedle base can be about 300 microns.

In some embodiments, the tip of the microneedles can be less than about 100 microns, less than about 75 microns, less than about 50 microns, less than about 40 microns, less than about 30 microns, or less than about 20 microns. In some embodiments, the tip of each of the microneedles can be about 10 microns.

The microneedle array can comprise a plurality of microneedles, wherein the bases of microneedles are arranged in any suitable two-dimensional pattern. The microneedles can be arranged in a regular array (e.g., a square, rectangular, circular, oval or other shaped pattern), such as shown in FIG. 3A, wherein the distance between individual microneedles remains the same or varies in a repeating fashion, or in an irregular array (e.g., wherein the distance between individual microneedles varies in no recognizable repeating fashion). In some embodiments, the array can be a regular 11 microneedle×11 microneedle square array.

In some embodiments, such as shown in FIG. 1A, the array can further include one or more base layers attached to the base of each of the microneedles. In some embodiments, the base layer comprises a suitable absorbent material to aid in the removal of oil, dead cells and related cellular matter (e.g., pus and dead cell debris) from the active disease site. Thus, the base layer can comprise a crosslinked polymer (e.g., a crosslinked hydrophilic polymer), which can be the same or different as the polymer of the crosslinked polymer that comprises embedded antibiotic, and an absorbent additive. In some embodiments, the additive comprises diatomaceous earth (DE). However, other absorbent additives can also be used, e.g., in place of, or in combination with, the DE. Other suitable absorbent additives include, but are not limited to, aluminum silicate, aluminum starch octenylsuccinate, amylodextrin, attapulgite, bentonite, calamine, calcium silicate, cellulose, chalk, active charcoal, colloidal oatmeal, corn flour, corn starch, cyclodextrin, dextrin, dimethylimidazolidinone corn starch, fuller's earth, hectorite, hydrated silica, silica, kaolin, loess, magnesium aluminum silicate, magnesium carbonate, magnesium hydroxide, magnesium oxide, magnesium silicate, magnesium trisilicate, maltodextrin, microcrystalline cellulose, montmorillonite, oat bran, oat flour, oat meal, potato starch, talc, wheat powder, zeolite, and the like. Suitable loading levels of the absorbent additive can be, for example, between about 0.01% and about 30% by weight (e.g., about 0.01, 0.05, 0.1, 0.5, 1.0, 2.5, 5.0, 7.5, 10, 12, 14, 16, 18, 20, 25, or 30% by weight). In some embodiments, the base layer comprises about 10% by weight of the absorbent additive. In some embodiments, the base layer polymer comprises crosslinked methacrylated hyaluronic acid (m-HA).

The array can also include other layers attached on the back of the base layer (i.e., on the side of the base layer opposite to the side attached to the base of the microneedles). For instance, in some embodiments, the array can further include a protective backing layer to protect the other array components from moisture or other external contaminants as well as mechanical injury, such as from scratching. In some embodiments, the protective backing layer comprises a water-resistant or water-proof plastic film. In some embodiments, the array can include an adhesive backing layer (e.g., so that the array can be attached to another material or to a subject being treated) or a tinted layer (e.g., tinted with a color selected to match a human skin color so that the array can blend better with the skin color of the subject being treated with a patch comprising the array).

In some embodiments, the array can be affixed to a suitable applicator device, such as a plastic or fabric substrate that can be held in the hand to manually apply the array to an affected area of the skin. Thus, in some embodiments, the array is affixed, e.g., using a suitable adhesive, to an applicator device, such as, but not limited to a wand, a swab (e.g., a cotton swab), a wipe, a pad, or a towelette.

In some embodiments, the presently disclosed subject matter provides a skin patch comprising the microneedle array of the presently disclosed subject matter. In some embodiments, the skin patch can comprise one or more backing layers (e.g., to protect the microneedle array from moisture or other contaminants or physical insult (e.g., scratches). Thus, in some embodiments a water-resistant or water-proof plastic film can be attached to the base layer of the array. In some embodiments, the microneedle array can comprise a layer that extends outward from the array (e.g., coplanar to the base of the array) that comprises a skin-compatible adhesive for aiding in the attachment of the array to the skin. In some embodiments, the patch can further include a decorative or tinted backing layer (e.g., to make the patch less noticeable when attached to the skin surface of a subject being treated with the patch).

In some embodiments, the presently disclosed subject matter provides a method of treating a skin disease, disorder or condition using the presently disclosed compositions or a microneedle, microneedle array or skin patch comprising the composition. In some embodiments, the skin disease is an inflammatory and/or infection-related skin disease. In some embodiments, the skin disease is acne. In some embodiments, the method comprises contacting an acne outbreak site or other active skin disease skin surface with a microneedle array or skin patch of the presently disclosed subject matter.

For example, in some embodiments, the presently disclosed subject matter provides a method of delivering an acne treatment agent to a subject in need thereof, the method comprising administering a microneedle array of the presently disclosed subject matter to the subject. The array can be contacted to the subject's skin at the site of an acne outbreak. In some embodiments, the array can be attached to an applicator device such as a wand, a swab (see, for example, FIG. 3B), a wipe, a pad, or a towelette (e.g., comprising a plastic and/or fabric surface) that can be held in the hand and applied to an outbreak site for a relatively short period of time (e.g., a few seconds or minutes), thereby delivering the acne treatment agent to the outbreak site. In some embodiments, the array can be contacted to the site manually for a period of time between about 1 second and about 10 minutes (e.g., for about 10, 20, 30, 40, 50, 60, or 90 seconds, or for about 2, 3, 4, 5, 6, 7, 8, 9, or 10 minutes). The treatment can be repeated at regular intervals, e.g. once or twice a day, or as needed.

In some embodiments, the microneedle array can be part of a skin patch or other device that can be affixed to the skin surface (e.g., via the use of a suitable adhesive in a backing layer of the patch) such that the acne treatment can be delivered continuously to an outbreak site for a period of several minutes, hours, or days. Thus, in some embodiments, the patch can be affixed to the affected site for a period of time ranging from about 15 minutes to about 7 days (e.g., about 1, 4, 8, 12, 18 or 24 hours or about 2, 3, 4, 5, 6, or 7 days). The treatment can be repeated one or more times per day, week or month, as needed.

In some embodiments, the subject treated according to the presently disclosed subject matter is a human subject, although it is to be understood that the methods described herein are effective with respect to all mammals.

The presently disclosed microneedle arrays can release CDM or another antibiotic or acne therapeutic agent in a bioresponsive (e.g., inflammation-responsive and/or ROS-responsive) manner. In some embodiments, the release rate of the CDM or other therapeutic is dependent upon the concentration of ROS coming into contact with the array (e.g., the release rate is faster when the array is in contact with higher concentrations of ROS).

In some embodiments, the array can be studied after contact with a subject's skin. For example, in some embodiments, biological fluids absorbed by the microneedle and/or absorbent additive can be extracted and their content assayed to confirm a disease diagnosis or to determine how well the treatment is working, e.g., if the level of bacteria present in the biological fluids and/or the level of inflammation-related biomolecules is being reduced over time. Thus, in some embodiments, the materials of the microneedle itself (e.g., the swollen crosslinked hydrophilic polymer/hydrogel) can absorb samples (such as cells, bacteria, viral particles, toxins, biomarkers of infection and/or inflammation, etc.). Added absorbents (e.g., in a microneedle array base layer or in the microneedle itself) can also be employed for extracting tissue fluid.

In some embodiments, the presently disclosed subject matter provides a method of preparing a microneedle array comprising a plurality of microneedles comprising a biocompatible polymeric network comprising a biodegradable polymer or a bioresponsive crosslinked hydrophilic polymer and an antibiotic. In some embodiments, the method comprises providing a mold comprising one or more microneedle (MN)-shaped microcavities. In some embodiments, the microcavities can be approximately conical or pyramidal in shape. In some embodiments, the microcavities have a depth of between about 300 and about 900 micrometers. In some embodiments, the mold comprises silicone.

Figure 6:
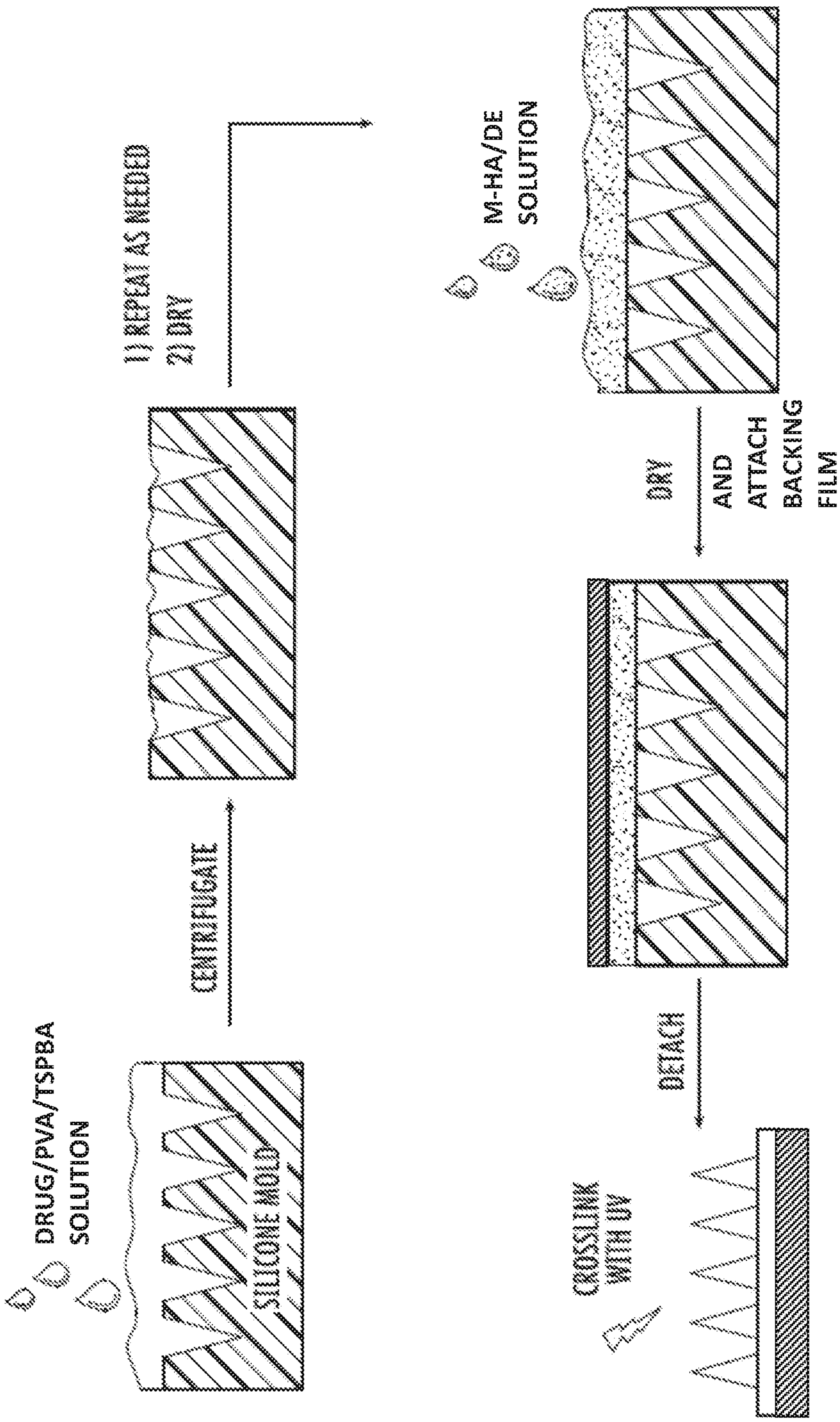
FIG. 6 is a schematic drawing of an exemplary process for preparing a reactive oxygen species (ROS)-responsive microneedle (MN) array patch of the presently disclosed subject matter using a silicone mold.

As shown in FIG. 6, in some embodiments, the microneedles can be prepared by dropping a solution (e.g., a diluted aqueous solution) comprising the hydrophilic polymer, bioresponsive crosslinking agent, and antibiotic (or antibiotic-loaded carrier, e.g., an antibiotic-loaded liposome, polymersome, nanoparticle or microparticle), such as a Drug/PVA/TSPBA solution, into the mold comprising MN-shaped cavities. The mold can then be maintained (e.g., under vacuum) for a period of time to more fully deposit the solution in the cavities. In some embodiments, the mold can be centrifuged to further condense the polymer solution and form the crosslinked polymer network encapsulating the antibiotic. The dropping, maintaining, and/or centrifuging steps can optionally be repeated as necessary to more fully fill the MN cavities.

Continuing with FIG. 6, in some embodiments, following the filling of the MN cavities, a second solution can be dropped onto the mold to form a base layer. In some embodiments, the second solution comprises a cross-linkable biocompatible polymer, such as, but limited to acrylate-modified hyaluronic acid (m-HA), a suitable crosslinking agent (e.g., N,N'-methylenebis(acrylamide) (MBA)), a photoinitiator (e.g., Irgacure 2959), and an absorbent (e.g., DE). The mold can then be dried (e.g., in a vacuum desiccator) and removed from the mold. In some embodiments, UV radiation can be applied to the mold to crosslink the base layer. In some embodiments, such as shown in FIG. 6, a backing layer (e.g., a plastic film) can be attached to the base layer prior to removal of the array from the mold.

In some embodiments, the presently disclosed subject matter provides a ROS-responsive antibiotic hydrogel comprising: (a) a crosslinked hydrophilic polymer, wherein said crosslinked hydrophilic polymer comprises a hydrophilic polymer, optionally PVA or a copolymer thereof, crosslinked via a plurality of ROS-responsive linkages, wherein each of the ROS-responsive linkages comprises one or more bond that is cleavable in the presence of a ROS, optionally wherein the ROS is a peroxide; and (b) an antibiotic or antibiotic-loaded carrier embedded in the biocompatible polymeric network, optionally wherein the antibiotic is clindamycin (CDM). In some embodiments, the presently disclosed subject matter provides a microneedle, a microneedle array, or a skin patch comprising the hydrogel. In some embodiments, the hydrogel or a MN-array prepared therefrom is administered to a skin surface of a subject in need of treatment for acne or another inflammatory/infectious skin disease.

In some embodiments, the presently disclosed subject matter provides compositions and microneedle arrays that are antibiotic-free, but which contain a skin repair agent, a wound healing agent, and/or an absorbent, e.g., diatomaceous earth. Such compositions and arrays can be similar to those described above containing an antibiotic or antibiotic loaded carrier. Thus, for example, the compositions can comprise a biocompatible polymeric network comprising (i) a biodegradable polymer (e.g., a polyester) or (ii) a crosslinked hydrophilic polymer wherein the crosslinked hydrophilic polymer comprises a hydrophilic polymer crosslinked with a plurality of bioresponsive linkages. Skin repair agents or wound healing agents can optionally be embedded in the biocompatible polymeric network.

In some embodiments, the presently disclosed subject matter provides a microneedle array that comprises an absorbent material, but which is free of an antibiotic or other drug. In some embodiments, the array can comprise microneedles comprising a biodegradable or bioresponsive crosslinked polymer. Such arrays can be used to help to more quickly relieve skin infection and/or speed skin healing at inflammatory/infectious skin disease-affected skin sites by absorbing and removing oil, dead cells, and/or related cellular matter (e.g., pus and dead cell debris). The absorbed cellular debris and/or pus can also be collected from the array after use for analysis of the inflammatory/infectious skin disease and/or the treatment progress thereof, e.g., by looking for molecules associated with an infectious agent and/or molecules associated with the inflammatory response.

Accordingly, in some embodiments, the presently disclosed subject matter provides a microneedle array comprising: (a) a plurality of microneedles comprising a biocompatible polymeric network comprising (i) a biodegradable polymer, optionally wherein the biodegradable polymer comprises a polyester, or (ii) a crosslinked hydrophilic polymer, wherein said crosslinked hydrophilic polymer comprises a hydrophilic polymer crosslinked via a plurality of bioresponsive linkages; (b) a base layer to which a base of each of said plurality of microneedles is attached and wherein said base layer comprises a crosslinked polymer; and (c) an absorbent. The absorbent can be present in the microneedles and/or the base layer. In some embodiments, the absorbent is present in the base layer (e.g., embedded in the base layer), e.g., to collect materials from the skin released after contact with the microneedles. In such embodiments, the array can be kept in contact with the skin for a relatively longer period of time (e.g., an hour or more) while the microneedles slowly degrade and then the base layer comprising the absorbent and absorbed materials can be removed. In some embodiments, the absorbent can be present in the microneedles and the array can be left in contact with the skin for a shorter period of time (e.g., a few seconds or a few minutes) and removed while the microneedles are still relatively intact to remove the absorbent and absorbed materials.

In some embodiments, each of said plurality of microneedles has a length of between about 20 and about 1000 micrometers (e.g., about 25, 50, 100, 150, 200, 250, 300, 400, 450, 500, 550, 600, 650, 700, 750, 800, 850, 900, 950, or about 1000 microns). In some embodiments, each of the plurality of microneedles has a length of between about 500 microns and about 700 microns. In some embodiments, each of the plurality of microneedles has a length of about 600 micrometers.

In some embodiments, each microneedle can have an approximately conical or pyramidal shape. In some embodiments, the base of each microneedle can be between about 10 and about 600 microns (e.g., about 20, 50, 75, 100, 150, 200, 250, 300, 350, 400, 450, 500, 550, or about 600 microns) in diameter. In some embodiments, the diameter of each microneedle base can be between about 200 and about 400 microns. In some embodiments, the diameter of each microneedle base can be about 300 microns.

In some embodiments, the tip of the microneedles can be less than about 100 microns, less than about 75 microns, less than about 50 microns, less than about 40 microns, less than about 30 microns, or less than about 20 microns. In some embodiments, the tip of each of the microneedles can be about 10 microns.

As with the antibiotic-containing microarrays described above, the microneedle array can comprise a plurality of microneedles, wherein the bases of microneedles are arranged in any suitable two-dimensional pattern. The microneedles can be arranged in a regular array (e.g., a square, rectangular, circular, oval or other shaped pattern), wherein the distance between individual microneedles remains the same or varies in a repeating fashion, or in an irregular array (e.g., wherein the distance between individual microneedles varies in no recognizable repeating fashion). In some embodiments, the array can be a regular 11 microneedle×11 microneedle square array.

In some embodiments, the plurality of microneedles comprise a crosslinked hydrophilic polymer crosslinked via a plurality of bioresponsive linkages. In some embodiments, one or more of the plurality of bioresponsive linkages is an inflammation-responsive linkage formed between the hydrophilic polymer and a crosslinking agent, wherein each inflammation-responsive linkage contains one or more chemical bond that is cleavable or otherwise sensitive to one or more conditions associated with inflammation. In some embodiments, the one or more conditions associated with inflammation are selected from the group comprising an increased concentration of reactive oxygen species (ROS); low pH, optionally a pH of below about 6; hypoxia; and an increased concentration of esterases or other enzymes and/or small biomolecules associated with inflammation.

In some embodiments, the hydrophilic polymer is selected from the group comprising polyvinyl alcohol (PVA); a polysaccharide (e.g., cellulose), hyaluronic acid (HA), dextran, alginate, cellulose, or a derivative thereof; a poly(amino acid), such as poly-L-lysine, poly-L-glutamic acid (PGS) or poly-L-serine; a protein or hydrophilic polypeptide, optionally gelatin; and a poly(alkylene glycol), optionally a poly(ethylene glycol) (PEG), polypropylene glycol (PPG), or a poly(ethylene oxide) (PEO); and linear or branched copolymers and block copolymers thereof. In some embodiments, the hydrophilic polymer is PVA or a copolymer thereof. In some embodiments, the PVA or other polymer has a weight average molecular weight ($M_w$) of between about 10 kDa and about 200 kDa (e.g., about 10, 25, 50, 75, 100, 125, 150, 175, or about 200 kDa). In some embodiments, the PVA has a $M_w$ of about 72 kDa.

In some embodiments, the inflammation-responsive linkages can comprise one or more ester or carbamate groups that can be cleaved by an esterase or via acid-catalyzed hydrolysis (i.e., in a low pH aqueous environment). In some embodiments, the inflammation responsive linkage comprises a ROS-responsive linkage. In some embodiments, the ROS-responsive linkage comprises an aryl boronic ester, a phenyl boronic acid or ester, a thioether, a selenium bond (e.g., a diselenium bond), a tellurium bond, a thioketal, and/or an aryl oxalate ester. In some embodiments, the ROS-responsive linkage comprises an aryl boronic ester. For instance, the bivalent linkage resulting from reaction of the crosslinking agent and the polymer can have a structure of, for example:

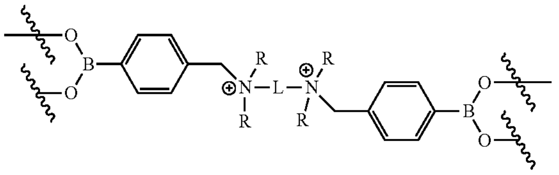

wherein each R is independently $C_1$-$C_6$ alkyl, and L is alkylene, aralkylene, or arylene. In some embodiments, each R is methyl. In some embodiments, L is propylene (i.e., $—CH_2CH_2CH_2—$). In some embodiments, the linker can be provided in the form of a pharmaceutically acceptable salt and include one or two anions (e.g., a halide anion) to balance the charge of the aminium ions. The linkage can be the result of the reaction of hydroxyl groups on a polymer chain with the hydroxyl groups of boronic acid moieties in the crosslinking agent. Thus, for instance, each of the four oxygen atoms of the structure shown above can be covalently attached to carbon atoms in a polymer chain. In some embodiments, the crosslinked hydrophilic polymeric network is prepared by crosslinking PVA with $N^1$-(4-bromobenzyl)-$N^3$-(4-bromophenyl)-$N^1$,$N^1$,$N^3$,$N^3$-tetramethylpropane-1,3-diaminium (TSPBA).

Any suitable material crosslinked polymer material can be used for the base layer. In some embodiments, the base layer comprises a crosslinked hydrophilic polymer. The polymer of the base layer can be the same or different from the polymer of the microneedles described above. In some embodiments, the base layer polymer comprises crosslinked methacrylated hyaluronic acid (m-HA).

Any suitable absorbent material can be used. In some embodiments, the additive comprises diatomaceous earth (DE). However, other absorbent additives can also be used, e.g., in place of, or in combination with, the DE. Other suitable absorbent additives include, but are not limited to, aluminum silicate, aluminum starch octenylsuccinate, amylodextrin, attapulgite, bentonite, calamine, calcium silicate, cellulose, chalk, active charcoal, colloidal oatmeal, corn flour, corn starch, cyclodextrin, dextrin, dimethylimidazolidinone corn starch, fuller's earth, hectorite, hydrated silica, silica, kaolin, loess, magnesium aluminum silicate, magnesium carbonate, magnesium hydroxide, magnesium oxide, magnesium silicate, magnesium trisilicate, maltodextrin, microcrystalline cellulose, montmorillonite, oat bran, oat flour, oat meal, potato starch, talc, wheat powder, zeolite, and the like. Suitable loading levels of the absorbent (e.g., in the microneedles and/or the base layer) can be, for example, between about 0.01% and about 30% by weight (e.g., about 0.01, 0.05, 0.1, 0.5, 1.0, 2.5, 5.0, 7.5, 10, 12, 14, 16, 18, 20, 25, or 30% by weight). In some embodiments, the base layer comprises about 10% by weight of the absorbent.

The array can also include other layers attached on the back of the base layer (i.e., on the side of the base layer opposite to the side attached to the base of the microneedles). For instance, in some embodiments, the array can further include a protective backing layer to protect the other array components from moisture or other external contaminants as well as mechanical injury, such as from scratching. In some embodiments, the protective backing layer comprises a water-resistant or water-proof plastic film. In some embodiments, the array can include an adhesive backing layer (e.g., so that the array can be attached to another material or to a subject being treated) or a tinted layer (e.g., tinted with a color selected to match a human skin color so that the array can blend better with the skin color of the subject being treated with a patch comprising the array).

In some embodiments, the array can be affixed to a suitable applicator device, such as a plastic or fabric substrate that can be held in the hand to manually apply the array to an affected area of the skin. Thus, in some embodiments, the array is affixed, e.g., using a suitable adhesive, to an applicator device, such as, but not limited to a wand, a swab (e.g., a cotton swab), a wipe, a pad, or a towelette.

In some embodiments, the presently disclosed subject matter provides a skin patch comprising an antibiotic-free absorbent-containing microneedle array of the presently disclosed subject matter. In some embodiments, the skin patch can comprise one or more backing layers (e.g., to protect the microneedle array from moisture or other contaminants or physical insult (e.g., scratches). Thus, in some embodiments a water-resistant or water-proof plastic film can be attached to the base layer of the array. In some embodiments, the microneedle array can comprise a layer that extends outward from the array (e.g., coplanar to the base of the array) that comprises a skin-compatible adhesive for aiding in the attachment of the array to the skin. In some embodiments, the patch can further include a decorative or tinted backing layer (e.g., to make the patch less noticeable when attached to the skin surface of a subject being treated with the patch). The antibiotic-free microneedle arrays can be prepared by methods similar to those described above for the antibiotic-containing microneedle arrays, only omitting the inclusion of an antibiotic.

In some embodiments, the presently disclosed subject matter provides a method of treating a skin disease, disorder or condition using the antibiotic-free microneedle array or skin patch comprising an absorbent. In some embodiments, the skin disease is an inflammatory and/or infection-related skin disease. In some embodiments, the skin disease is acne. In some embodiments, the method comprises contacting an acne outbreak site or other active skin disease skin surface with the microneedle array or skin patch. In some embodiments, the array can be contacted to the site manually or using an applicator (e.g., a wand) for a period of time between about 1 second and about 10 minutes (e.g., for about 10, 20, 30, 40, 50, 60, or 90 seconds, or for about 2, 3, 4, 5, 6, 7, 8, 9, or 10 minutes). Array application can be repeated at regular intervals, e.g. once or twice a day, or as needed to collect oils, dead cells, and/or other materials. In some embodiments, the array or patch can be affixed to an affected site for a period of time ranging from about 15 minutes to about 7 days (e.g., about 1, 4, 8, 12, 18 or 24 hours or about 2, 3, 4, 5, 6, or 7 days). Application can be repeated one or more times per day, week or month, as needed. In some embodiments, the method provides for a faster rate of resolution of the skin condition and/or faster skin healing related to the skin condition.

EXAMPLES

The following examples are included to further illustrate various embodiments of the presently disclosed subject matter. However, those of ordinary skill in the art should, in light of the present disclosure, appreciate that many changes can be made in the specific embodiments which are disclosed and still obtain a like or similar result without departing from the spirit and scope of the presently disclosed subject matter.

Example 1

Preparation of Ros-Responsive Hydrogel

All chemicals were purchased from Sigma-Aldrich (St. Louis, Missouri, United States of America) unless otherwise specified and were used as received. The deionized water was prepared by a Millipore NanoPure purification system (MilliporeSigma, Burlington, Massachusetts, United States of America; resistivity higher than 18.2 MΩ $cm^{-1}$).

Synthesis of ROS-Responsive Crosslinker (TSPBA):

4-(Bromomethyl) phenylboronic acid (1 g, 4.6 mmol) and N,N,N',N'-tetramethyl-1,3-propanediamine (0.2 g, 1.5 mmol) were dissolved in dimethylformamide (DMF; 40 mL) and the solution was stirred at 60° C. for 24 h. Afterward, the mixture was poured into tetrahydrofuran (THF, 100 mL), filtrated, and washed with THF (3×20 mL). After drying under vacuum overnight, pure TSPBA (0.6 g, yield 70%) was obtained. $^{1}$H-NMR (300 MHz, $D_2O$, δ): 7.677 (d, 4H), 7.395 (d, 4H), 4.409 (s, 4H), 3.232 (t, 4H), 2.936 (s, 6H), 2.81 (m, 2H). The synthetic route and structure of the TSPBA linker is shown below in Scheme 1.

Scheme 1. Synthesis of TSPBA linker.

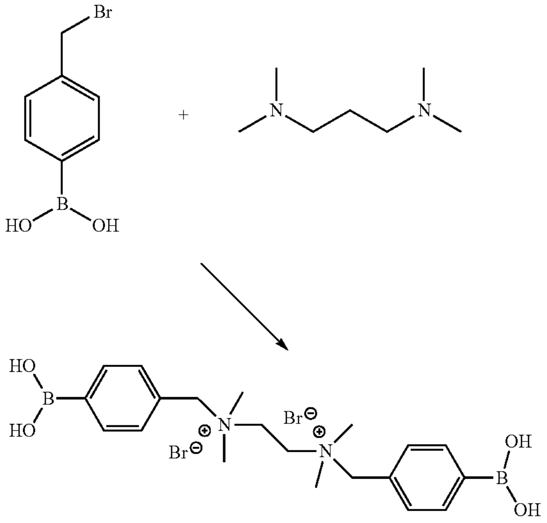

Preparation of RR-PVA Hydrogels:

PVA (MW: 72 kDa, 98% hydrolyzed) were dissolved in deionized (D) water to obtain 10 wt % clear PVA solution. The RR-PVA hydrogel was formed by mixing PVA and TSPBA (5 wt % in $H_2O$) together at a ratio of 3:1. A predetermined amount of drug or dye was added to the PVA aqueous solution to prepare drug/dye-loaded hydrogel.

Preparation of NR-PVA Hydrogels:

Non-responsive (NR) PVA network was prepared by crosslinking methacrylated PVA (m-PVA) with N, N'-methylenebis(acrylamide) (MBA) at a ratio of 3:1 in the presence of photoinitiator (Irgacure 2959) under ultraviolet (UV) light. m-PVA was synthesized following a previous reported method. See Zhang et al. (Small 2018, DOI: 10.1002/smll.201704181).

Example 2

In Vitro Results with Ros-Responsive Hydrogel

In Vitro Release Profiles:

The in vitro release profiles of CDM from RR-PVA gel were evaluated through incubation of the hydrogel in 12 mL PBS buffer (NaCl, 137 mM; KCl, 2.7 mM; $Na_2HPO_4$, 10 mM; $KH_2PO_4$, 2 mM; pH 7.4) at 37° C. on an orbital shaker, to which $H_2O_2$ was added to reach 1 mM concentration. At predetermined time points, the concentrations of CDM in the supernatant were determined by high performance liquid chromatography (HPLC). Samples were analyzed at 205 nanometers (nm) on a Zorbax Eclipse Plus RRHD C18 column (2.1×50 mm, 1.8 μm particle size) (Agilent Technologies, Santa Clara, Calif., United States of America) using an isocratic mobile phase consisting of 80% water (HPLC grade with 0.1% v/v trifluoroacetic acid) and 20% acetonitrile (HPLC grade with 0.1% v/v trifluoroacetic acid). The cumulative release (%) is expressed as the percent of total drug released over time.

In Vitro Antibacterial Effect:

*P. acnes* (ATCC 6919) (American Type Culture Collection, Manassas, Va., United States of America) were cultured on reinforced clostridial medium (RCM) at 37° C. in an anaerobic environment. The stock culture of *P. acnes* was transferred to RCM broth and incubated anaerobically at 37° C. overnight. The cultures were later used to prepare bacterial suspensions ($2×10^8$ colony forming units (CFUs)/mL). The antimicrobial efficiency against *P. acnes* was determined by incubating *P. acnes* with the incubation medium with RR-PVA gel in the absence of $H_2O_2$, CDM solution (5 μg/mL), or the incubation medium with RR-PVA gel in the presence of $H_2O_2$ for 5 hours, while *P. acnes* in PBS was used as a negative control. Following incubation, the samples were diluted $1:10^3$ in PBS, and 10 μL of each sample was spotted on RCM agar plates. The samples were incubated at 37° C. under an anaerobic condition for another 72 h. The CFU of *P. acnes* was quantified.

Figure 2B:
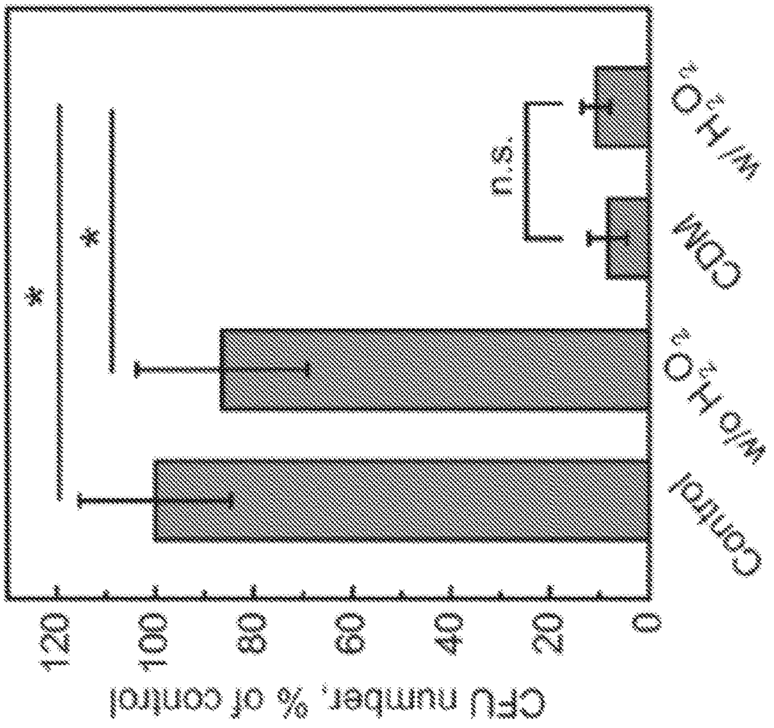
FIG. 2B is a graph showing the quantitative analysis of colony-forming units (CFUs) in a *P. acnes* suspension cultured for 72 hours on a reinforced clostridial medium (RCM) agar plate with, from left to right: the addition of either phosphate buffered saline (PBS) as a control; the addition of an incubation medium with a reactive oxygen species (ROS)-responsive polyvinyl alcohol (RR-PVA) gel loaded with clindamycin (CDM) but without hydrogen peroxide (w/o $H_2O_2$), the addition of a free CDM solution, or the addition of an incubation medium with a RR-PVA gel loaded with CDM and comprising hydrogen peroxide (w/$H_2O_2$). Error bars indicate standard deviation (s.d.) (n=3), two-tailed Student's t-test, *P<0.05.
Figure 2A:
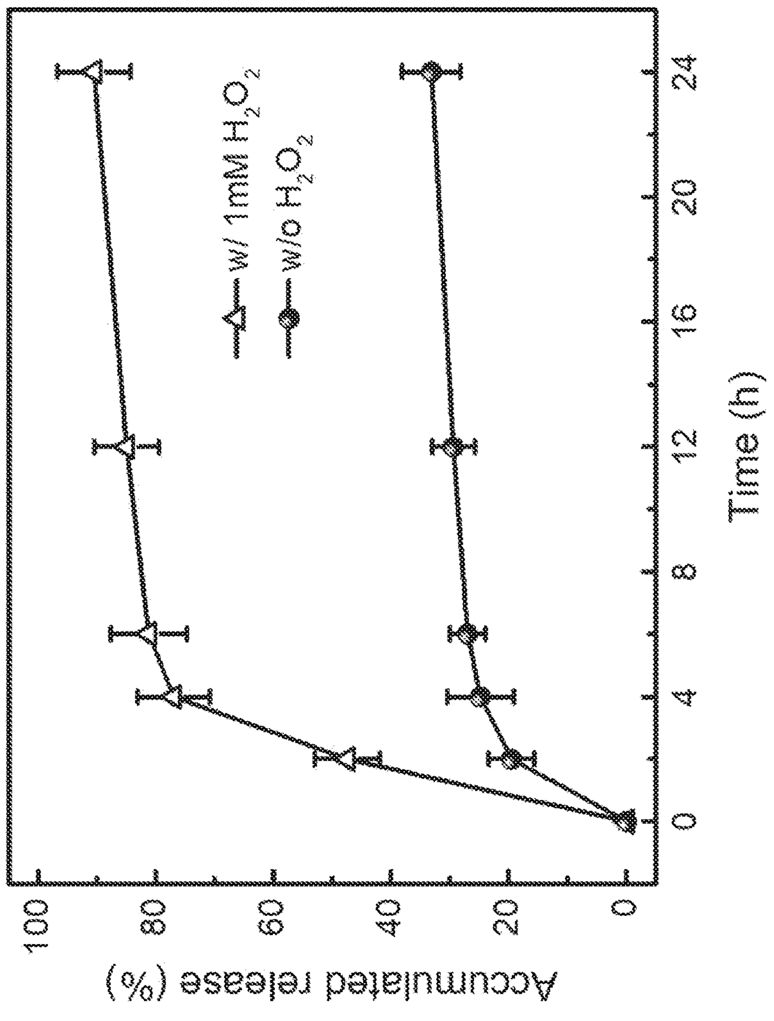
FIG. 2A is a graph showing the accumulated release profile (accumulated release (in percentage (%)) versus time (in hours (h))) of clindamycin (CDM) from a reactive oxygen species (ROS)-responsive polyvinyl alcohol gel in the presence of 1 millimolar hydrogen peroxide (w/1 mM $H_2O_2$, unfilled triangles) or without hydrogen peroxide (w/o $H_2O_2$, filled circles). Error bars indicate standard deviation (s.d.) (n=3).
Figure 2C:
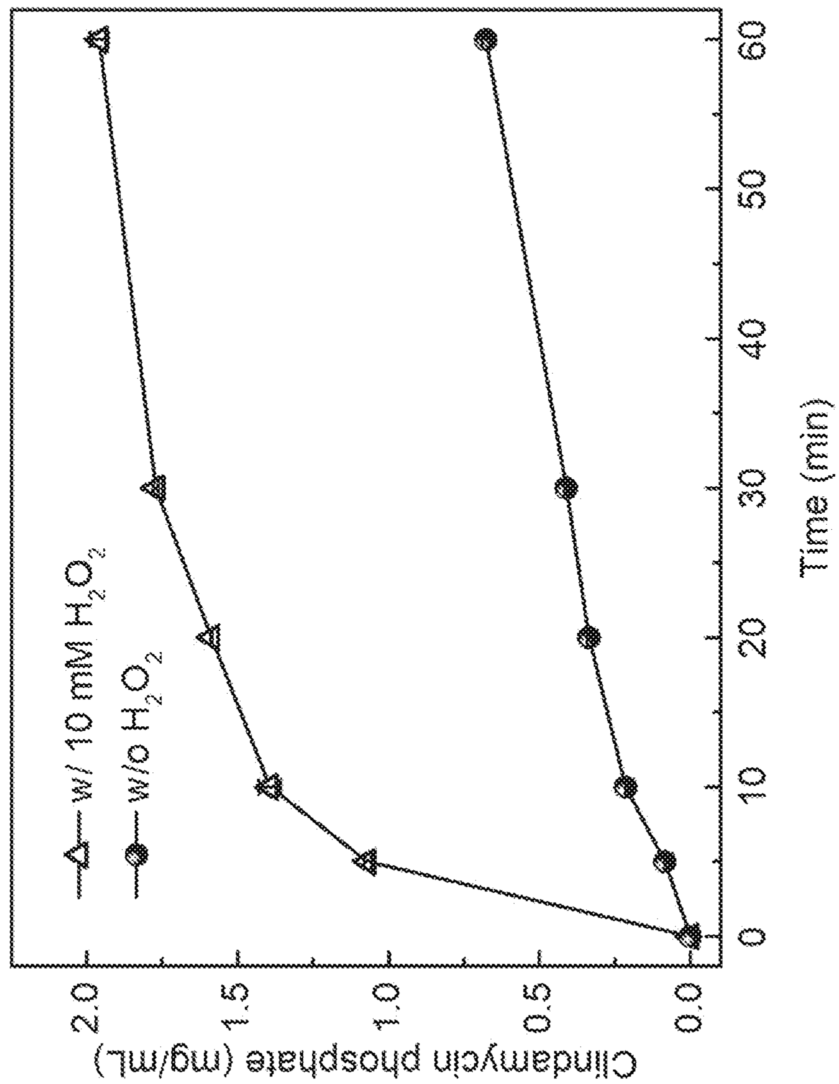
FIG. 2C is a graph showing the accumulated release profile (accumulated release (in milligrams per milliliter (mg/mL)) versus time (in minutes (min))) of clindamycin phosphate from a reactive oxygen species (ROS)-responsive polyvinyl alcohol gel in the presence of 10 millimolar hydrogen peroxide (w/10 mM $H_2O_2$, unfilled triangles) or without hydrogen peroxide (w/o $H_2O_2$, filled circles).

When incubating with the PBS solution containing 1 mM $H_2O_2$, the ROS-triggered sustained drug release was also detected from the RR-PVA/CDM gel. See FIG. 2A. In addition, the RR-PVA gel showed faster degradation and drug release rate under a higher $H_2O_2$ concentration at 10 mM (see FIG. 2C), further confirming the ROS-dependent degradation of the RR-PVA gel.

Figure 1B:
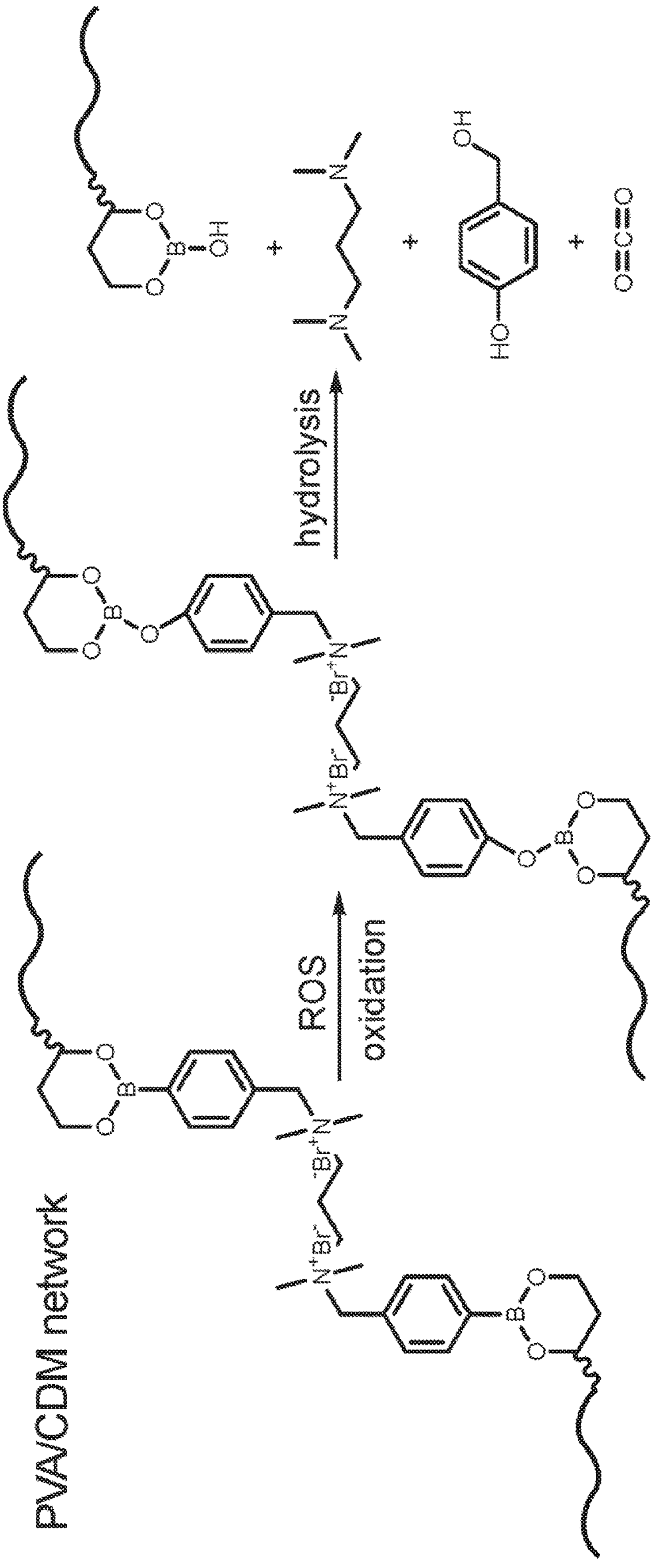
FIG. 1B is a schematic drawing of the chemical mechanism of the degradation of the clindamycin (CDM)-loaded polyvinyl alcohol (PVA) network (PVA/CDM network) described in FIG. 1A. More particularly, reactive oxygen species (ROS) trigger an initial oxidation reaction of phenyl boronic acid-based cross-linking moieties present in the PVA/CDM network, leading to hydrolysis of the crosslinking moiety.

Discussion:

ROS-responsive gel was first prepared as described in Example 1 by crosslinking PVA using a linker comprising two phenylboronic acid groups (see Scheme 1, above). The linker can be cleaved by ROS through oxidation and further hydrolysis. See FIG. 1B. Clindamycin (CDM), a common antibiotic for acne treatment (see Lookingbill et al., J. Am. Acad. Dermatol., 1997, 37, 590), was entrapped in the RR-PVA matrix for *P. acnes* elimination. To substantiate the responsiveness of the crosslinker, RR-PVA hydrogel was incubated in phosphate buffered saline (PBS) buffer (pH 7.4) comprising 1 mM $H_2O_2$ at 37° C. Rapid degradation of the RR-PVA hydrogel was observed due to the oxidation of the crosslinkers. See FIG. 2A. The non-responsive (NR) PVA gel without the ROS-sensitive linker was stable in the presence of $H_2O_2$. There was no obvious change in morphology or size of the RR-PVA gel in the buffer without $H_2O_2$, indicating the high stability of the RR-PVA matrix.

In vitro antibacterial effect was evaluated by culturing *P. acnes* with media comprising RR-PVA/CDM gel and hydrogen peroxide. The $H_2O_2$-contained incubation media with RR-PVA/CDM gel displayed significant inhibitory effect on bacterial growth comparing with the control group treated with PBS solution. See FIG. 2B. In contrast, the incubation media without $H_2O_2$ showed insignificant effect on the growth of bacterial. Without being bound to any one theory, this lack of effect is believed to be due to limited drug diffusion from RR-PVA/CDM gel in the absence of $H_2O_2$. Collectively, these results demonstrated that the drug release from RR-PVA was in a ROS-mediated manner, which could achieve an on-demand treatment effect for inflammatory acne therapy.

Example 3

Preparation of Ros-Responsive Microneedle Patch

Fabrication of ROS-Responsive (RR) Microneedle Patch:

All the MN patches in this study were prepared using the uniform silicone molds from Blueacre Technology Ltd (Dundalk, Ireland). There are 11×11 needle array in the mold, where each needle has a height of 600 μm and a round base of 300 μm in diameter. The space from tip-to-tip is 600 μm. First, the PVA MNs were formed by pipetting premixed PVA (3 wt %)/TSPBA (3 wt %) (ratio 3:1) solution (400 μL) onto the MN mold surface. The molds were kept under vacuum (600 mmHg) for 30 min to allow the solution deposit into the MN cavities. Afterwards, the covered mold was centrifuged for 20 min at 500 rpm using a Hettich Universal 32R centrifuge (Hettich GmbH & Co. KG, Tuttlingen, Germany) to condense the PVA network in the MNs. Drug-loaded MNs were fabricated by adding a predetermined amount of drug in PVA/TSPBA solution at the first step. The non-responsive (NR) microneedles were prepared by changing the MN solution to a mixed solution consisting of m-PVA (3 wt %), MBA (1 wt %), and photoinitiator (Irgacure 2959, 0.5 wt %). For CDM MN, 4 wt % HA containing CDM were used to form the MNs for fast release of drug. Then the base of the patch was formed by adding 3 mL m-HA solution (4 wt %) containing diatomaceous earth (DE) (0.4 wt %), MBA (0.2%) and 2959 (0.1 wt %) into the prepared micromold reservoir and drying at room temperature under vacuum desiccator for 3 days. m-HA was synthesized following the previous reported method. See Zhang et al., ACS Nano 2017, 11, 9223. After complete desiccation, the MN patch was carefully detached from the silicone mold and stored in a sealed six well container for later study. Finally, a transparent plastic film (3M™ TEGADERM™, 3M Company, Maplewood, Minn., United States of America) was sealed on top of the MN patch during in vivo administration. The morphology of the MNs was characterized via a FEI Verios 460L field-emission scanning electron microscope (FESEM) (FEI, Hillsboro, Oregon, United States of America).

Microneedle Mechanical Strength Test:

The mechanical strength of MN was determined by pressing MNs against a stainless-steel plate at a speed of 1 μm/s on a 30 G tensile testing machine (MTS Systems Corporation, Eden Prairie, Minn., United States of America). The failure force of the microneedle was recorded as the force at which the needle began to buckle.

Oil Adsorption Capacity Test of Diatomaceous Earth (DE):

The oil adsorption capacity of DE was determined by mixing free acid solution with 1 g DE until no more free acid can be adsorbed at room temperature. The ratio of the weight of free acid and DE was calculated.

Figure 3C:
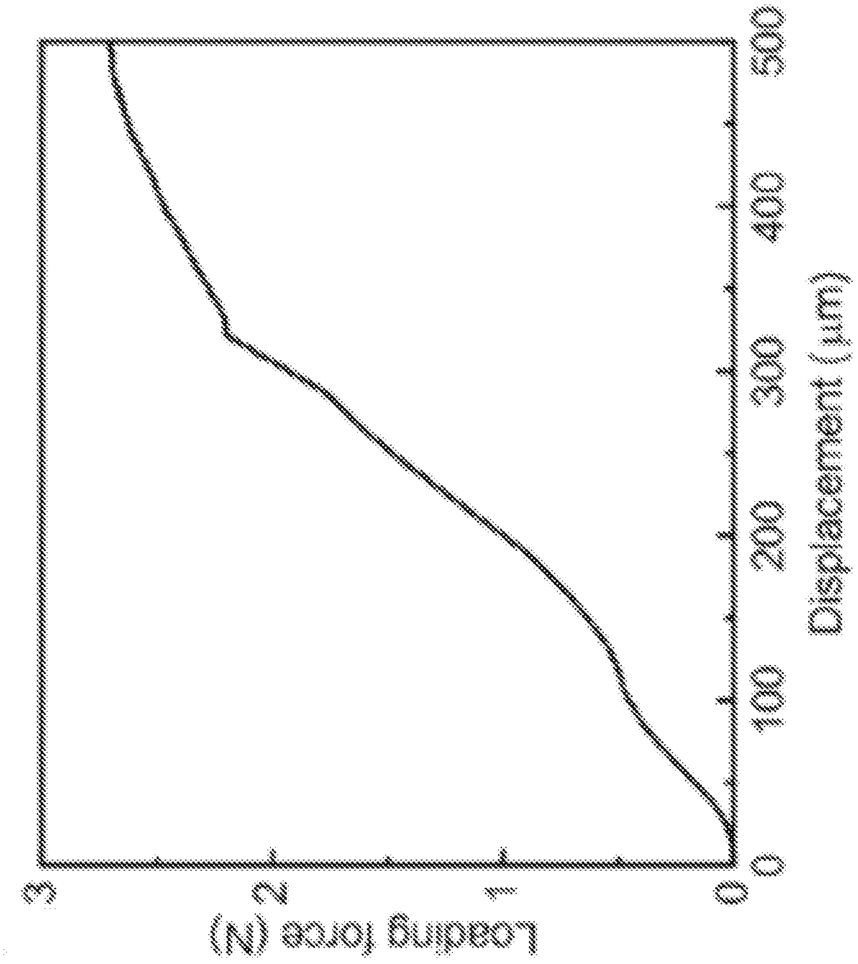
FIG. 3C is a graph of the mechanical behavior (force per needle (in Newtons (N)) versus displacement (in microns (μm))) of a reactive oxygen species-response polyvinyl alcohol/clindamycin (PVA/CDM) network microneedle (MN) of the presently disclosed subject matter.
Figure 5B:
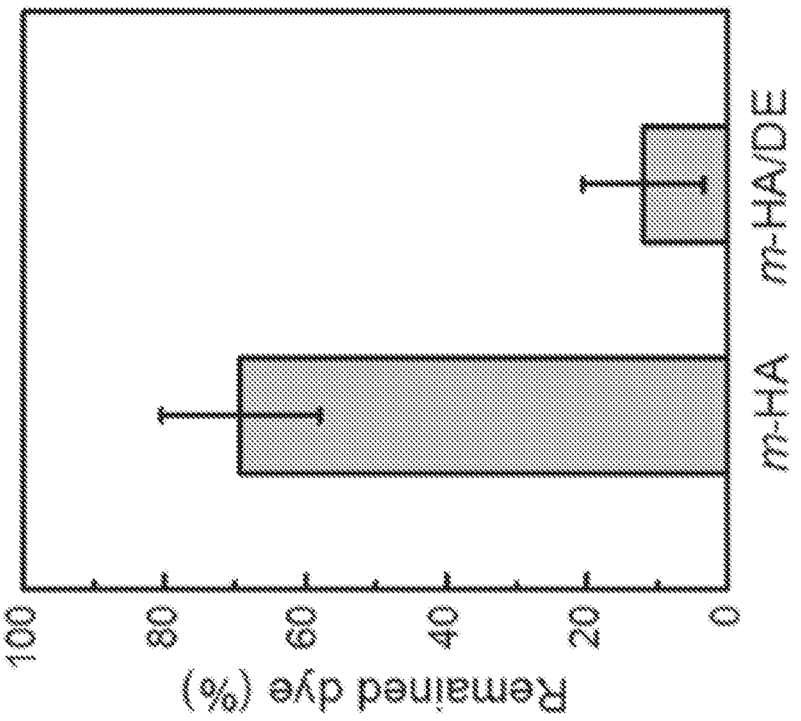
FIG. 5B is a graph showing the quantitative analysis of the adsorption of rhodamine B (RhB) dye by an acrylate-modified hyaluronic acid (m-HA) film or a m-HA film loaded with diatomaceous earth (m-HA/DE). The RhB and mHA or m-HA/DE films were incubated in a phosphate buffered saline (PBS) solution at 37 degrees Celsius (° C.) for 30 minutes. Data is provided as the percentage (%) of dye remaining in the solution.
Figure 5A:
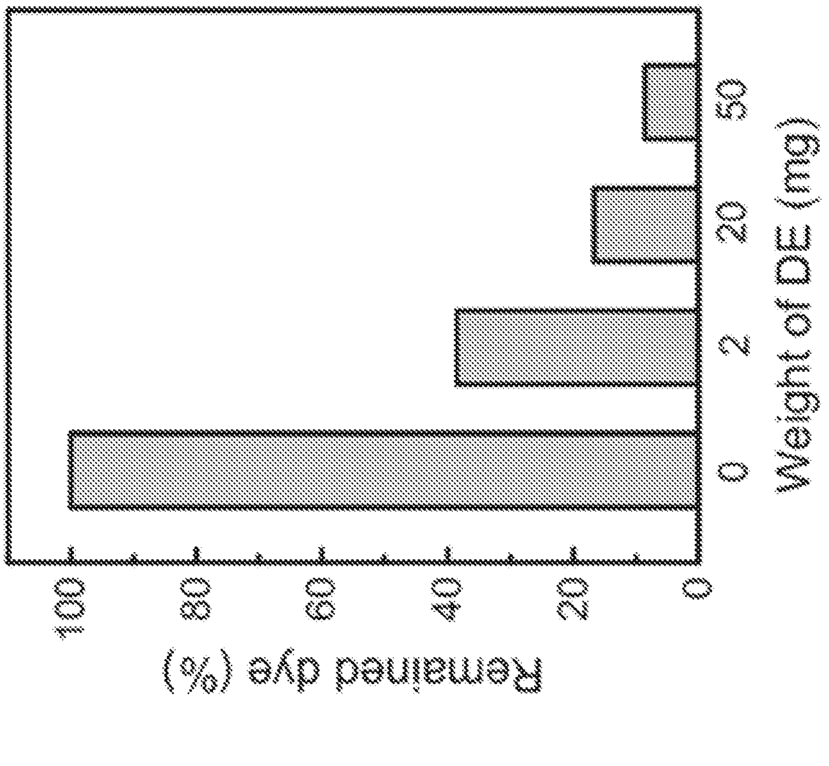
FIG. 5A is a graph showing the quantitative analysis of the adsorption of dye in an aqueous solution by varying amounts of diatomaceous earth (DE). The graph shows the amount of remaining dye (as a percentage (%)), i.e., rhodamine B (RhB), in an aqueous solution comprising different amounts (0, 2, 20 or 50 milligrams (mg)) of DE.

Discussion:

For further efficient drug delivery into acne underneath the skin, a MN-array patch was fabricated through a micromolding method. Briefly, the drug containing responsive MNs were first formed by depositing diluted PVA/CDM solution with ROS-responsive crosslinker into the tip region of a silicone micro-scale mold under a vacuum condition and then condensing by centrifugation. As shown in FIG. 3A, each MN was of a conical shape, with a base diameter of 300 μm and a height of 600 μm. The mechanical strength of each MN was determined as 2.2 N (see FIG. 3C), which sufficiently enables skin penetration without breaking. See Zhana et al., ACS Nano 2017, 11, 9223; Zhang et al., Adv. Mater. 2017, 29; and Lee et al., Biomaterials 2008, 29, 2113. Afterward, a layer of m-HA/DE matrix was integrated as the supporting substrate. HA was chosen considering its excellent biocompatibility and biodegradability (see Koqan et al., Biotechnol. Lett. 2007, 29, 17) and DE was additionally doped for its physical adsorption property. See A-Ghouti et al., J. Environ. Manage. 2003, 69, 229. DE, which typically comprises 87-91% silicon dioxide (see Tsai et al., J. Colloid Interface Sci. 2006, 297, 749), has been widely applied as an absorbent because of its porous structure. It turned out to have ~95% oil adsorption capability, which was 3-fold higher than the activated carbon (~32%). See Okiel et al., Egypt J. Pet. 2011, 20, 9. The adsorption capability of small molecules, such as a fluorescent dye, was also demonstrated. See FIGS. 5A and 5B. Therefore, the DE could be useful to adsorb pus and purulent exudates in acne. The obtained device was arranged in a 11×11 array with an interval of 600 μm from tip to tip on a 7×7 $mm^2$ patch. Additionally, the patch can also be applied on a cotton swab for an alternative temporary administration method. See FIG. 3B.

Example 4

In Vivo Results

In Vivo Acne Treatment Efficacy Evaluation:

Eight-week old male Balb/c nude mice ordered from Qinglongshan Animal Center (Nanjing, China) were used. To examine the bactericidal effect of MN patches, *P. acnes* ($2\times10^6$ CFUs/mL) was intradermally injected into the back skin of each mouse to establish the acne vulgaris animal model. Mice were divided into seven groups with seven mice in each group. Six-group of mice were induced by *P. acnes* injection and treated with different formulations for six days: CDM cream (1% v/v CDM in 4% v/v HA solution), RR-MN patches, blank MN patches, CDM MN patches, NR-MN patches (CDM dosage: 0.4 mg/patch). The swelling volumes of the acne were measured using a micro-caliper every day during the treatment period.

Histological Analysis of Infected Skin:

The skin tissue samples were excised from the mice 6 days after treatment and were fixed in 10% formalin for 18 h. Then, the tissues were embedded in paraffin, cut into 50 μm sections, and stained using hematoxylin and eosin (H&E) for histological analysis.

Statistical Analysis:

All results were presented as Mean±SD.

Statistical analysis was performed using Student's t-test or one-way ANOVA. With a p value<0.05, the differences between experimental groups and control groups were considered statistically significant.

Discussion:

The in vivo antibacterial performance of MN patches was investigated in a *P. acnes*-induced inflammation mouse model. The Balb/c nude mice were randomly divided into seven groups (n=7), with six groups infected by *P. acnes* via intradermal injection into the skin on the back, and one group injected with PBS solution as a positive control group (labeled as normal). No swelling was detected in the PBS-injection mice, while a considerable volume raise was observed one day after *P. acnes* infection.

Figure 4A:
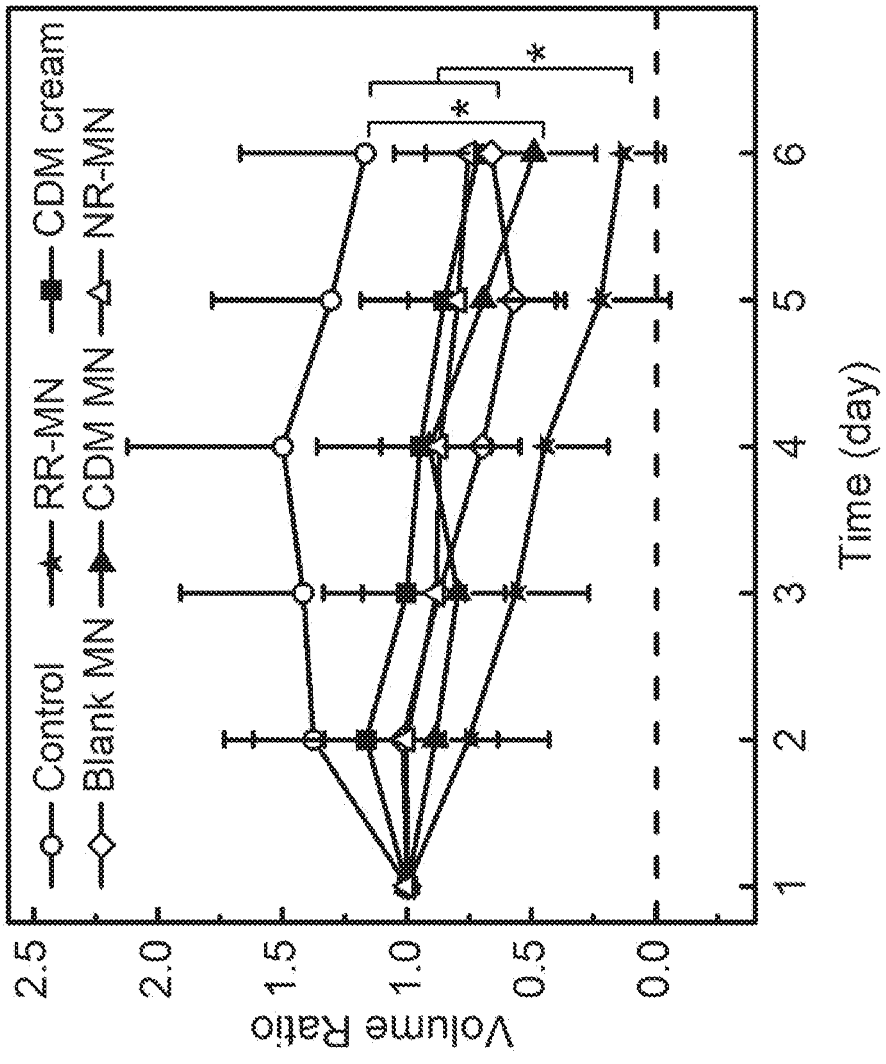
FIG. 4A is a graph showing the swelling volume size (measured as a volume ratio of volume on a particular treatment day/volume on treatment day 1) in the back skins of *P. acnes*-induced mice during treatment for up to 6 days with: a reactive oxygen species (ROS)-responsive clindamycin (CDM)-loaded polyvinyl alcohol (PVA) microneedle patch (RR-MN, filled stars); a 1 weight percent (wt %) CDM cream (CDM cream, filled squares); blank microneedles without CDM (blank MN, unfilled diamonds); a CDM-loaded hyaluronic acid (HA) microneedle patch (CDM-MN, filled triangles); or a non-responsive PVA/CDM microneedle patch (NR-MN, unfilled triangles). In addition, one group of mice were chosen as a negative control and received no treatment (Control, unfilled circles). Two-tailed Student's t-test *P<0.05, **P<0.01 for RR-MN treated group compared with all other groups; n.s.=no significant difference.

Then the *P. acnes*-infected mice were treated with different formulations to evaluate the treatment efficiency. One group was chosen as negative control without treatment (control), another one group was administered with 1 wt % CDM cream, and other four groups were respectively administered with ROS-responsive PVA/CDM microneedle patches (RR-MN), CDM loading HA microneedle patches (CDM MN), non-responsive PVA/CDM microneedle patches (NR-MN), and blank microneedle patches without CDM (blank MN) (CDM dose: 0.4 mg per mouse). The volume size of the swollen skin was monitored every day during the treatment. See FIG. 4A. Without treatment, the skin of mice in the control group continued to swell up to day 4. In contrast, the skin in the group treated with RR-MN shrank in size approximately 90% after administration and part of the swell even started to disappear on day 5, suggesting the effective inhibitory effect of acne growth by RR-MN. The skin of the group treated with CDM cream barely decreased in size of the swollen skin, and neither did the skin of the groups treated with blank MN or NR-MN. Without being bound to any one theory, the slight skin size reduction caused by blank MN or NR-MN can be attributed to the physical adsorption of pus and cell debris by the patches through the microchannels generated by MNs. Although the CDM MN delivered drug into the infected skin, there was no significant inhibition of the acne growth, which is believed due to the fast release and clearance of the drug. In comparison, the RR-MN allowed a sustained antibiotic release within the acne area and resulted in the enhanced bactericidal effect.

Figure 4B:
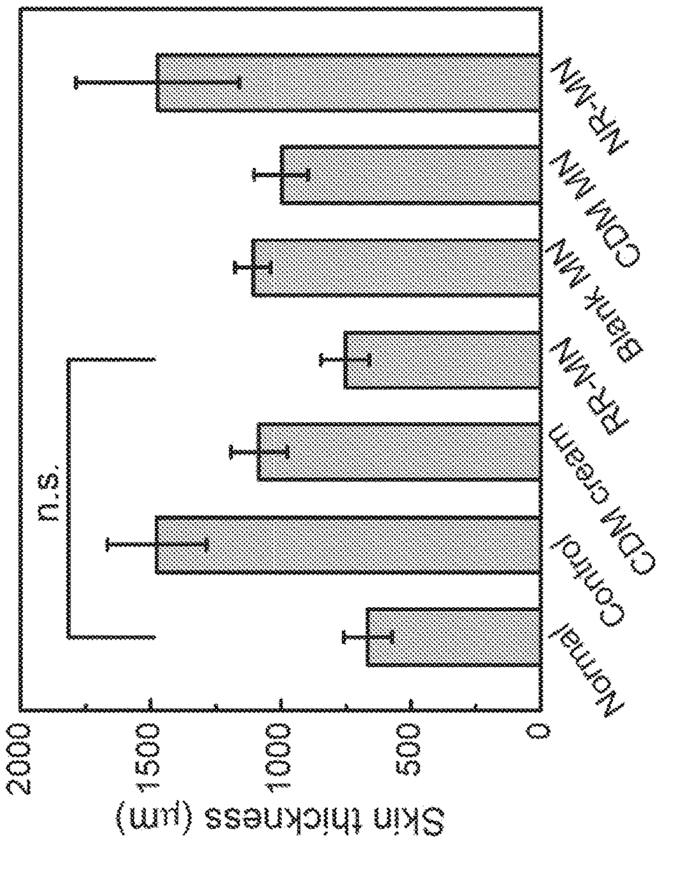
FIG. 4B is a graph showing the quantitative analysis of the thickness (in microns (μm)) of the skin from mice in each treatment group described for FIG. 4A. Data for untreated mice without acne (Normal) is also shown. Error bars indicate standard deviation (s.d.) (n=7).
Figure 4C:
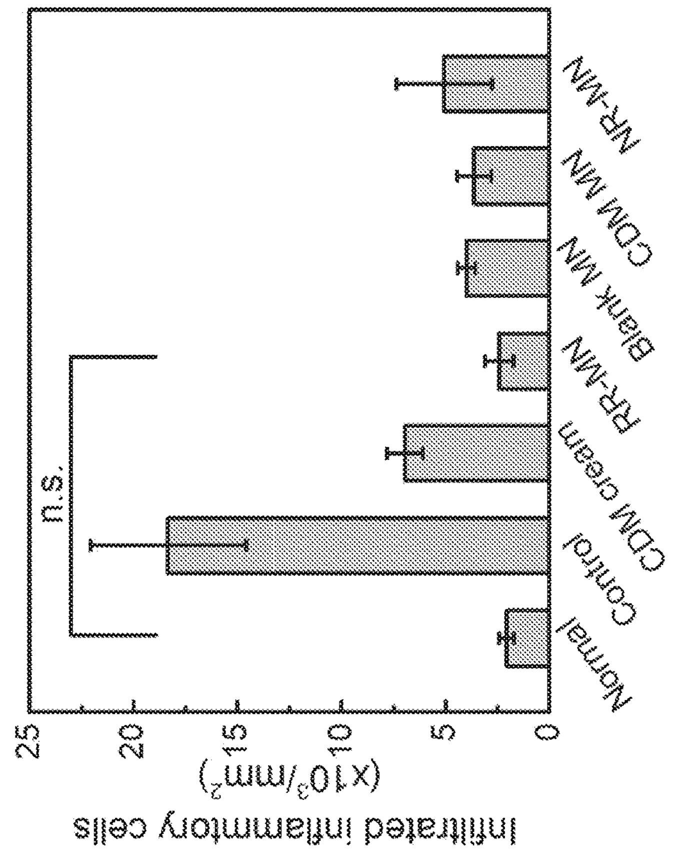
FIG. 4C is a graph showing the quantitative analysis of infiltrated inflammation cells (thousands of cells per square millimeter ($\times10^3/mm^2$)) in the skin of mice from each treatment group described for FIG. 4A. Data for untreated mice without acne (Normal) is also shown. Error bars indicate standard deviation (s.d.) (n=7); n.s.=no significant difference.

After a period of six-day treatment, the mice were sacrificed and the skin tissues with the acne were excised for histological analysis. Consistent with the acne growth curve, the clinical inflammatory lesions were significantly improved in the skin tissues treated with RR-MN, compared to other treated groups as observed via Haemotoxylin and Eosin (H&E) staining. The number of the microcomedone-like cysts in the upper dermis above the focus of inflammation in the RR-MN-treated group also decreased to an extent similar to that in the normal skin tissues. The quantitative measurement of skin thickness demonstrated that there was no significant difference between the skin treated with RR-MN and normal skin thickness (see FIG. 4B), validating the efficacy of the RR-MN. In addition, the number of infiltrated inflammatory cells into the dermis also dramatically decreased in the skin treated with RR-MN patches compared to that in *P. acnes*-induced skin without treatment. See FIG. 4C. CDM cream did not effectively inhibit the skin thickening or inflammation in comparison with RR-MN-treated groups, implying insufficient drug penetration into the dermis. The skin-related effects of the various treatments are summarized in Table 1, below. These results indicated that transdermal administration of the RR-MN patch effectively suppressed *P. acnes*-induced inflammation, without causing noticeable side effects in the surrounding skin tissue.

TABLE 1

Skin Effects of Different Treatments.

| | CDM cream | RR-MN | Blank MN | CDM MN | NR-MN |
|---|---|---|---|---|---|
| Clinical inflammation | Prominent/dense | mild | moderate | moderate | Prominent/dense |
| Epidermal thickening | moderate | mild | moderate | moderate | Prominent/dense |
| Microcomedone-like cysts | Prominent/dense | mild | moderate | moderate | moderate |
| Inflammatory cells | moderate | mild | mild | mild | moderate |

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A composition comprising:

(a) a biocompatible polymeric network comprising a crosslinked hydrophilic polymer, wherein said crosslinked hydrophilic polymer comprises a hydrophilic polymer crosslinked via a plurality of reactive oxygen species (ROS)-responsive linkages; and (b) an antibiotic or antibiotic-loaded carrier embedded in the biocompatible polymeric network, which provides sustained release of the antibiotic, wherein one or more ROS-responsive linkage comprises a structure:

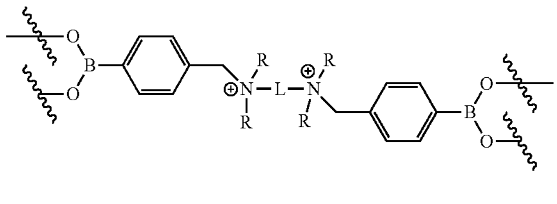, or a pharmaceutically acceptable salt thereof, wherein:

each R is independently C1-C6 alkyl, and

L is alkylene, aralkylene, or arylene.

2. The composition of claim 1, wherein the antibiotic is selected from the group consisting of clindamycin (CDM) or another lincosamide antibiotic;

tetracycline; doxycycline; minocycline; limecycline; trimethroprim; cotrimoxazole; erythromycin;
and metronidazole or another nitroimidazole antibiotic.

3. The composition of claim 1, wherein the composition further comprises a non-antibiotic therapeutic agent.

4. The composition of claim 1, wherein the hydrophilic polymer is selected from the group consisting of polyvinyl alcohol (PVA); a polysaccharide; a poly (amino acid); a protein or hydrophilic polypeptide; and a poly (alkylene glycol); and linear or branched copolymers and block copolymers thereof.

5. The composition of claim 1, wherein the hydrophilic polymer is PVA or a copolymer thereof.

6. The composition of claim 1, wherein the hydrophilic polymer has a weight average molecular weight (Mw) of between about 10 kilodaltons (kDa) and about 200 kDa.

7. The composition of claim 1, wherein the biocompatible polymeric network is prepared by crosslinking PVA with N1-(4-bromobenzyl)-N3-(4-bromophenyl)-N1,N1,N3,N3,-tetramethyl-propane-1,3-diaminium (TSPBA) in a molar ratio of between about 20:1 to about 1:5.

8. The composition of claim 1, wherein the composition comprises between about 0.1 weight % and about 50 weight % of the antibiotic.

9. The composition of claim 1, wherein the composition further comprises one or more additional treatment agent embedded in the biocompatible polymeric network.

10. A microneedle comprising the composition of claim 1.

11. A microneedle array comprising a plurality of microneedles of claim 10, optionally wherein each of said plurality of microneedles has a length of between about 20 and about 1000 micrometers, further optionally wherein each of the plurality of microneedles has a length of about 600 micrometers and/or a base diameter of about 300 micrometers.

12. The microneedle array of claim 11, wherein the base of each of said plurality of microneedles is attached to a base layer comprising a crosslinked polymer and an absorbent additive, optionally wherein said absorbent additive is diatomaceous earth (DE) and/or wherein said polymer is methacrylated hyaluronic acid.

13. The microneedle array of claim 12, wherein the base layer comprises about 10% by weight of the absorbent additive, optionally wherein the absorbent additive is selected from the group consisting of aluminum silicate, aluminum starch octenylsuccinate, amylodextrin, attapulgite, bentonite, calamine, calcium silicate, cellulose, chalk, active charcoal, colloidal oatmeal, corn starch, cyclodextrin, flour, corn dextrin, diatomaceous earth, dimethylimidazolidinone corn starch, fuller's earth, hectorite, hydrated silica, silica, kaolin, loess, magnesium aluminum silicate, magnesium carbonate, magnesium hydroxide, magnesium oxide, magnesium silicate, magnesium trisilicate, maltodextrin, microcrystalline cellulose, montmorillonite, oat bran, oat flour, oat meal, potato starch, talc, wheat powder, zeolite, and combinations thereof.

14. The microneedle array of claim 12, further comprising a protective backing layer attached to the base layer, optionally wherein the protective backing layer comprises a water-resistant or water-proof plastic film.

15. The microneedle array of claim 11, wherein the microneedle array is attached to an applicator device selected from the group consisting of a wand, a swab, a wipe, a pad, or a towelette.

16. A skin patch comprising the microneedle array of claim 11, optionally wherein said patch comprises a layer comprising a skin compatible adhesive.

17. A reactive oxygen species (ROS)-responsive antibiotic hydrogel comprising:

(a) a crosslinked hydrophilic polymeric network, wherein said crosslinked hydrophilic polymeric network comprises a hydrophilic polymer, optionally PVA or a copolymer thereof, crosslinked via a plurality of ROS-responsive linkages, wherein each of the ROS-responsive linkages comprises one or more bond that is cleavable in the presence of a ROS, optionally wherein the ROS is a peroxide; and (b) an antibiotic or antibiotic-loaded carrier embedded in the crosslinked hydrophilic polymeric network, optionally wherein the antibiotic is clindamycin.

18. A microneedle array comprising:

(a) a plurality of microneedles comprising a biocompatible polymeric network comprising (i) a biodegradable polymer, optionally wherein the biodegradable polymer comprises a polyester, or (ii) a crosslinked hydrophilic polymer, wherein said crosslinked hydrophilic polymer comprises a hydrophilic polymer crosslinked via a plurality of bioresponsive linkages, optionally wherein each of said plurality of microneedles has a length of between about 20 and about 1000 micrometers, further optionally wherein each of the plurality of microneedles has a length of about 600 micrometers and/or a base diameter of about 300 micrometers;

(b) a base layer to which a base of each of said plurality of microneedles is attached and wherein said base layer comprises a crosslinked polymer, optionally wherein the crosslinked polymer is methacrylated hyaluronic acid; and (c) an absorbent, optionally wherein the absorbent is present in the base layer.

19. The composition of claim 1, wherein the composition further comprises an absorbent additive.

20. The composition of claim 19, wherein the absorbent additive is diatomaceous earth.

21. The composition of claim 3, wherein the non-antibiotic therapeutic agent is selected from a benzoyl peroxide formulation; a retinoid; isotretinoin; an antiandrogen; salicylic acid; azelaic acid; an antimicrobial peptide; omiganan pentahydrochloride; an inhibitor of a pro-inflammatory skin lipid; a free fatty acid; a peroxisome proliferator-activated receptor (PPAR) modulator; and metaformin.

22. The composition of claim 4, wherein the hydrophilic polymer is selected from the group consisting of cellulose, hyaluronic acid (HA), dextran, alginate, poly-L-lysine, poly-L-glutamic acid (PGS), poly-L-serine, gelatin, poly (ethylene glycol) (PEG), polypropylene glycol (PPG), poly (ethylene oxide) (PEO) and linear or branched copolymers and block copolymers thereof.

23. The composition of claim 6, wherein the hydrophilic polymer is PVA with a Mw of about 72 kDa.

24. The composition of claim 1, wherein L is propylene.

25. The composition of claim 9, wherein the one or more additional treatment agent is a skin repair agent, a wound-healing agent, or an antimicrobial agent.

26. The composition of claim 7, wherein the biocompatible polymeric network is prepared by crosslinking PVA with N1-(4-bromobenzyl)-N3-(4-bromophenyl)-N1,N1,N3,N3,-tetramethyl-propane-1,3-diaminium (TSPBA) in a molar ratio of about 3:1.

* * * * *